(12) United States Patent
Harmer et al.

(10) Patent No.: US 12,193,806 B2
(45) Date of Patent: Jan. 14, 2025

(54) SYSTEMS AND METHODS FOR DETECTING MARKERS FOR SURGICAL GUIDANCE

(71) Applicant: ENDOMAGNETICS LTD, Cambridge (GB)

(72) Inventors: Quentin John Harmer, Cambridge (GB); Kevin Lorimer, Cambridge (GB); Matthew James Stephens, Cambridge (GB)

(73) Assignee: ENDOMAGNETICS LTD (GB)

( * ) Notice: Subject to any disclaimer, the term of this patent is extended or adjusted under 35 U.S.C. 154(b) by 147 days.

(21) Appl. No.: 18/013,839

(22) PCT Filed: Jul. 8, 2021

(86) PCT No.: PCT/GB2021/051750
§ 371 (c)(1),
(2) Date: Dec. 29, 2022

(87) PCT Pub. No.: WO2022/008922
PCT Pub. Date: Jan. 13, 2022

(65) Prior Publication Data
US 2023/0329578 A1     Oct. 19, 2023

(30) Foreign Application Priority Data
Jul. 8, 2020   (GB) ..................................... 2010470

(51) Int. Cl.
*A61B 5/06* (2006.01)
*A61B 18/00* (2006.01)
*A61B 34/20* (2016.01)

(52) U.S. Cl.
CPC .............. *A61B 5/064* (2013.01); *A61B 34/20* (2016.02); *A61B 2018/00297* (2013.01); *A61B 2034/2051* (2016.02)

(58) Field of Classification Search
None
See application file for complete search history.

(56) References Cited

U.S. PATENT DOCUMENTS

| | | | |
|---|---|---|---|
| 3,836,842 | A | 9/1974 | Zimmermann et al. |
| 9,713,437 | B2 | 7/2017 | Fullerton et al. |
| (Continued) | | | |

FOREIGN PATENT DOCUMENTS

| | | |
|---|---|---|
| JP | S56135351 | 10/1981 |
| JP | S56135352 | 10/1981 |
| (Continued) | | |

OTHER PUBLICATIONS

PCT International Search Report and PCT Written Opinion for PCT International Application No. PCT/GB2021/051750; date of mailing Oct. 25, 2021; (15 pages).

*Primary Examiner* — Thomas S McCormack
(74) *Attorney, Agent, or Firm* — K&L GATES LLP

(57) ABSTRACT

A method for detecting a marker in a body, comprising receiving an input signal from a probe, where the input signal is generated by a probe in response to detecting a marker signal from the marker; determining a marker proximity value based on the input signal, the marker proximity value corresponds to a distance between the probe and the marker; generating a feedback signal for output by a user interface device based on the marker proximity value, and outputting feedback signal, wherein range of the marker proximity value is divided into predetermined distance bands; and wherein at least one parameter of the feedback signal, or a rate of change of the at least one parameter of the feedback signal in relation to marker proximity value, is varied discontinuously at a boundary between at least two adjacent bands. The feedback signal may be an audio signal and/or a haptic signal.

19 Claims, 10 Drawing Sheets

(56) References Cited

U.S. PATENT DOCUMENTS

| | | |
|---|---|---|
| 2003/0163040 A1 | 8/2003 | Gildenberg |
| 2008/0058637 A1 | 3/2008 | Fischell et al. |
| 2016/0051164 A1 | 2/2016 | Derichs et al. |
| 2018/0042517 A1 | 2/2018 | van der Weide et al. |

FOREIGN PATENT DOCUMENTS

| | | |
|---|---|---|
| WO | 2014/149183 A2 | 9/2014 |
| WO | 2017/059228 A1 | 4/2017 |

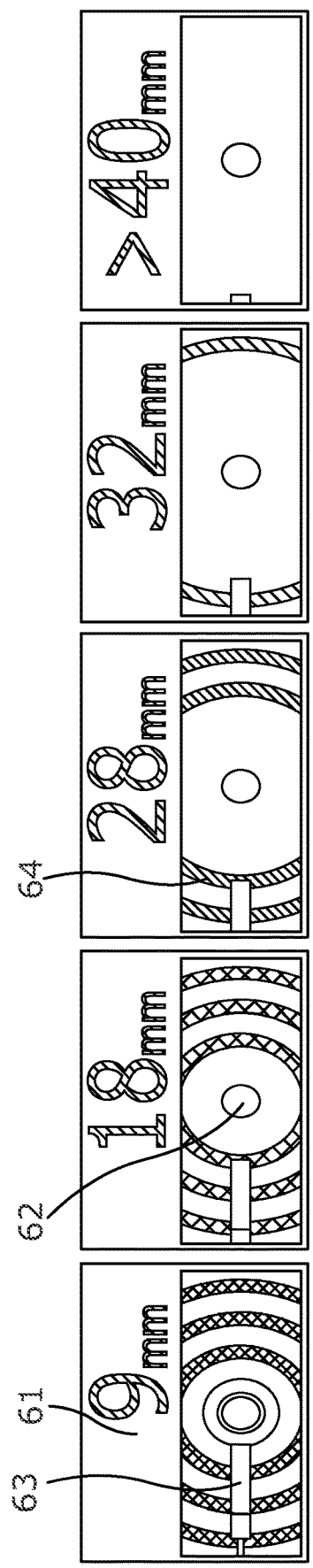
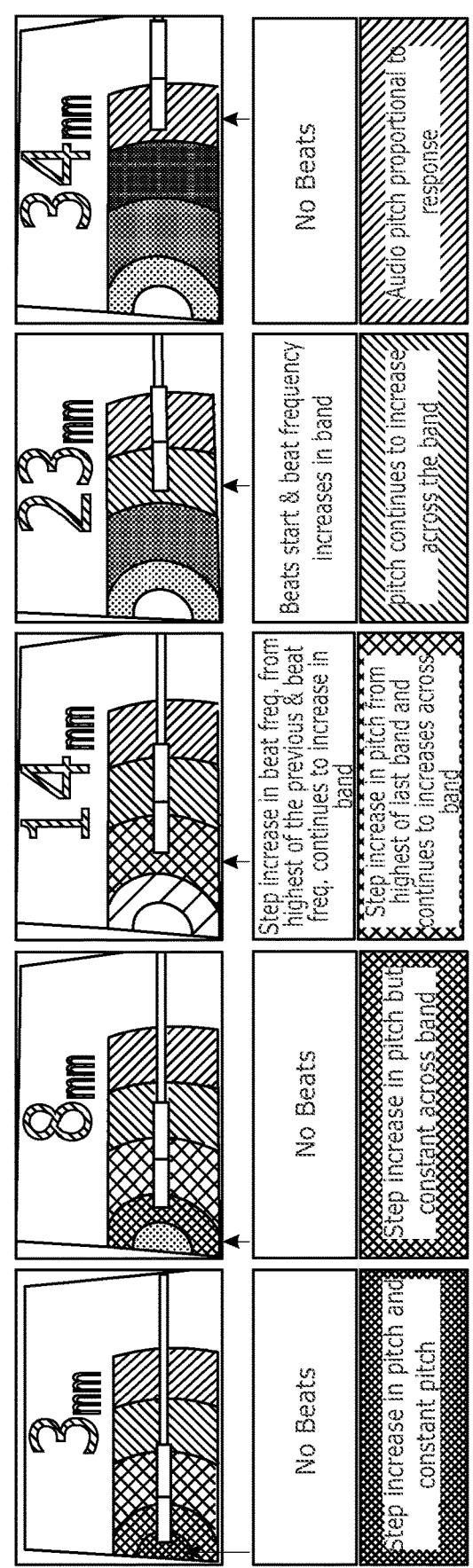

SYSTEMS AND METHODS FOR DETECTING MARKERS FOR SURGICAL GUIDANCE

CROSS REFERENCE TO RELATED APPLICATIONS

This is the national phase under 35 U.S.C. § 371 of International Application No. PCT/GB2021/051750 filed on Jul. 8, 2021, which claims priority to and the benefit of United Kingdom Application No. 2010470.9 filed on Jul. 8, 2020, the entire disclosures of each of which are incorporated by reference herein.

FIELD OF THE DISCLOSURE

This disclosure relates in general to the field of surgical guidance, more specifically to systems and methods for detecting markers that aid in locating a site in the body, for example, a lesion for surgical excision.

BACKGROUND

Markers are used to guide surgeons to a region of interest during a surgical procedure, where the site of interest is not physically visible or palpable, for example a small tumour that needs to be excised. Common clinical scenarios would be during a breast lumpectomy procedure, and cancerous or involved lymph node, lung lesion or similar.

There have been advances in the technologies used in breast localization to overcome the issues of wire guided localization, such as the issue of wire migration where the wire moves between its placement and surgical removal. If this occurs, the complete lesion may not be removed resulting in an additional surgery for the patient.

This issue can be overcome through the use of a placement of a detectable marker or seed. The marker may be placed during a biopsy or other surgical procedure at a site of interest in the body, for example a cancer lesion. Ideally, such a marker will be deployable through a narrow-gauge needle. The marker is placed under imaging guidance such as ultrasound or X-ray/mammography. During subsequent surgery, the marker is detected and localised using a handheld probe which provides audible, visual or other feedback to the surgeon to guide the surgery. Typically, the marker is excised along with the surrounding tissue.

A number of marker detection technologies are known for localizing lesions via detection of an implantable marker:
  US 2017/252124 (Cianna Medical) discloses a localization system which uses a combination of radio frequency (RF) electromagnetic signals and infra-red (IR) radiation to detect a marker in the form of an implantable reflector. The RF signals are also referred to interchangeably as radar signals.
  US 2015/264891 (Health Beacons) discloses a further system based on radio frequency identification (RFID) tags that have been used as identity markers for pets and livestock. The RFID tag is used to mark a lesion and an RFID probe is used to detect the marker.
  US20170095315 (Elucent Medical) discloses a tag detection system where the tag is activated by a magnetic field and the tag generates magnetic frequencies that are detectable by witness stations that detect the tag and communicate with a base unit.
  A further approach is discussed in the Applicant's earlier published patent applications (for example, WO 2011/067576, WO 2014/013235 and WO 2014/140567) and uses magnetic fields and a magnetic marker with high magnetic susceptibility. A handheld probe generates an alternating field which excites a magnetically responsive marker and detects the responding magnetic field.
  U.S. Pat. No. 7,881,775 discloses a radioactive seed localisation system where a seed containing a radioactive isotope is placed in the tumour and a handheld gamma probe is used to locate the seed and the tumour for excision.

The contents of all the aforementioned publications are incorporated herein by reference.

The markers may, for example, contain a radioactive isotope, and the probe may be a gamma probe. Such probes may inform the surgical user that the probe is pointing to the target and also if the probe/detector is getting closer or further away from the to the target site based on the increasing and decreasing gamma radiation detected. This detection is converted into both a count and audio (clicks/pulses etc.) signal, both of which are simply proportional to the detection. However, as the target site has an unknown amount of radioactivity (e.g. specific gamma radiation emitted from a target such as technetium in the node or radioactive iodine in a radioactive seed localization of a breast lesion), the specific value cannot provide significant proximity information. The increase and decrease of radioactivity must be used by the user to interpret and infer the range.

As disclosed in WO 2011/067576, WO 2014/032235 and WO 2014/140567, a magnetic marker with high magnetic susceptibility may be used. A handheld probe generates an alternating field which excites a magnetically responsive marker, and detects the responding magnetic field. An advantage of this approach relative to the radioactive seeds for the localization and surgical excision of a target site is that the marker provides a known response from the target which can be interpreted into a distance between the detector probe and the marker. Conventionally, a visual display of the detection system provides a distance, e.g., in millimetres, between the target and the detector. The audio response of these products remains similar to the gamma probe technology in that the audio output e.g., frequency of clicks, amplitude increases with a reduction in distance and related in a continuous manner to an increase in the detected signal. Such proportional audio output performs well to represent being relatively closer or further away from the marker, however, it is not readily interpretable by the user as a specific distance value. Hence the user is required to read the value to obtain the information desired.

There is therefore a need for feedback mechanisms for surgeons or other users to allow a more intuitive and accurate interpretation of signal via audio, visual or other means. The present invention aims to address this need and others.

SUMMARY OF THE DISCLOSURE

According to one aspect of the present disclosure there is provided a method of detecting a marker in a body, including receiving, by a processor, an input signal from a probe, where the input signal is generated by the probe in response to detecting a marker signal from the marker; determining, by the processor, a marker proximity value based on the input signal, where the marker proximity value corresponds to a distance between the probe and the marker; generating, by the processor and for output by a user interface device, at least one user feedback signal based on the marker proximity value; and outputting, by the user interface device, the generated feedback signal in a perceptible form. A range of the marker proximity value may be divided into a plurality of predetermined distance bands, and at least one parameter of the feedback signal or rate of change of the at least one parameter of the feedback signal with marker proximity value may be varied discontinuously at least at one boundary between two adjacent bands of the plurality of bands.

Suitably, the user interface device may comprise a speaker, and the feedback signal may comprise an audio signal. In use, therefore, the speaker may output the generated audio signal. Conveniently, the speaker may be accommodated within a base station.

Thus, in accordance with a particular aspect of the present disclosure there is provided a method of detecting a marker in a body, including receiving, by a processor, an input signal from a probe, where the input signal is generated by the probe in response to detecting a marker signal from the marker; determining, by the processor, a marker proximity value based on the input signal, where the marker proximity value corresponds to a distance between the probe and the marker; generating, by the processor and for output by a speaker, an audio signal based on the marker proximity value; and outputting, by the speaker, the generated audio signal. A range of the marker proximity value may be divided into a plurality of predetermined distance bands, and at least one parameter of the audio signal or rate of change of the at least one parameter of the audio signal with marker proximity value may be varied discontinuously at least at one boundary between two adjacent bands of the plurality of bands. Digital signal processing (DSP) may be used to generate and output the audio signal. The step of generating an audio signal and outputting the generated audio signal to a speaker may use a suitable soundcard of the kind known to those skilled in the art. The generated audio signal may be output by a soundcard. A digital to analogue convertor may be used to convert a digital generated signal into an analogue audio signal that can be output by the speaker.

In some embodiments, the user interface device may comprise a haptic feedback device, and the user feedback signal may comprise a haptic signal. In use, therefore, the haptic feedback device may output the generated haptic signal. In its broadest aspect the haptic feedback device may comprise any suitable kinaesthetic communication device that can create an experience of touch by applying forces, vibrations or motions to the user; for example by applying vibrations or transient pressure changes on the user's skin. In some embodiments, however, the haptic feedback device may comprise a selectively operable haptic actuator that is configured to generate discreet vibrations which are perceptible to a user. Conveniently, the haptic actuator or other haptic feedback device may be housed within the probe such that the haptic signal can be perceived by the user. For example, the haptic actuator may suitably be accommodated within a handle portion of the probe. In some embodiments, the haptic actuator may be mounted within a different unit which is placed in contact with the user in use. The haptic actuator may comprise any suitable haptic actuator which is known to those skilled in the art. Suitable haptic actuators include eccentric rotating mass (ERM) actuators, linear resonant actuators (LRA) and piezoelectric actuators.

Thus, in accordance with another particular aspect of the present disclosure there is provided a method of detecting a marker in a body, including receiving, by a processor, an input signal from a probe, where the input signal is generated by the probe in response to detecting a marker signal from the marker; determining, by the processor, a marker proximity value based on the input signal, where the marker proximity value corresponds to a distance between the probe and the marker; generating, by the processor and for output by a haptic actuator, a haptic signal based on the marker proximity value; and outputting, by the haptic actuator, the generated haptic signal. A range of the marker proximity value may be divided into a plurality of predetermined distance bands, and at least one parameter of the haptic signal or rate of change of the at least one parameter of the haptic signal with marker proximity value may be varied discontinuously at least at one boundary between two adjacent bands of the plurality of bands.

In some embodiments, the method of the disclosure may comprise generating two or more user feedback signals based on the marker proximity value and outputting, by two or more user interface devices, where the generated feedback signals is in perceptible forms. For example, the method may comprise generating an audio signal and a haptic signal based on the marker proximity value and outputting the generated audio and haptic signals by a speaker and a haptic actuator respectively. The same distance bands may be applied to the generated audio and haptic signals, and suitably, at least one parameter of the audio signal or haptic signal, or a rate of change of at least one parameter of the audio signal or haptic signal with marker proximity value, may be varied discontinuously at least at one boundary between two adjacent bands of the plurality of bands.

For each of the plurality of bands independently, the at least one parameter of the audio and/or haptic signal may be configured to (a) vary linearly with a change in the marker proximity value within the band, (b) vary non-linearly with a change in the marker proximity value within the band, or (c) remain constant with a change in the marker proximity value within the band.

In some embodiments, the rate of change of the at least one parameter of the audio and/or haptic signal with marker proximity value may vary discontinuously at the at least one boundary, while the at least one parameter may itself vary continuously across the at least one boundary.

Advantageously, a user feedback signal that has at least one parameter which varies, or has a rate of change which varies, discontinuously with marker proximity value at least at one boundary between two adjacent bands of the plurality of bands is that the discontinuous change may be more readily discerned by a user, thus clearly signalling to a surgeon, for example, who may be receiving lots of simultaneous information from different sources when a predetermined distance from the marker is reached. A discontinuous change or rate of change of an audio and/or haptic signal may therefore provide a clear indication to the user that a change in distance band has occurred.

The at least one parameter of the audio signal may be at least one of an amplitude, tone, pitch, timbre, beat frequency or beat pattern. The beat pattern may, for example, consist or occur in a beat duty, i.e. duty cycle, or a beat length.

The parameter of the haptic signal may be at least one of an amplitude, pulse frequency or pulse pattern. The pulse pattern may, for example, consist or occur in a pulse duty and/or pulse length.

For at least a first band, a first parameter of the audio and/or haptic signal may be varied continuously with a change in the marker proximity value within the band.

For at least a second band different from the first band, a second parameter of the audio and/or haptic signal may be varied continuously with a change in the marker proximity value within the band.

An advantage of continuous variation of an audio and/or haptic signal within a band is that a full or complete range of the signal spectrum may be used. Continuous variation of an audio and/or haptic signal within a first band and at least a second band is advantageous as this may allow use of a greater range of the signal spectrum.

Suitably, the at least one parameter of the audio and/or haptic may be a pulse frequency, a pulse length and/or a duty cycle of the audio signal. In some embodiments, the at least one parameter may be configured to remain substantially constant within at least one of the bands. Thus, in some embodiments, a first parameter of the audio and/or haptic signal may remain substantially constant within at least one of the bands. In some embodiments, the duty cycle of the signal may remain substantially constant within at least one of the bands. In some embodiments, the pulse length of the signal may remain substantially constant within at least one of the bands.

In some embodiments, a second parameter of the audio and/or haptic signal may also be varied in relation to the marker proximity value. Suitably, the second parameter of the audio and/or haptic signal may be an amplitude of the audio and/or haptic signal; for example a pitch and/or volume of the audio signal, or an amplitude of the haptic signal. The second parameter may be varied continuously within at least one of the bands. Suitably, the second parameter may increase with increased proximity to the marker. In some embodiments, the rate of change of the second parameter in relation to the marker proximity value may be varied discontinuously at at least one boundary between two adjacent bands of the plurality of bands. Thus, in some embodiments, the rate of change of pitch or volume of the audio signal may vary differently with marker proximity value as between at least two adjacent bands.

Advantageously, the second parameter may be varied continuously across the at least one boundary between two adjacent bands of the plurality of band. This may allow a maximal continuous rate of change of the second parameter to be provided across the range of marker proximity value covered by the at least two adjacent bands, thereby to afford maximal sensitivity to distance for a user. In some embodiments, the second parameter may be varied continuously across more than one, or all, of the boundaries between the plurality of bands. In some embodiments, the second parameter, e.g. the pitch of the audio signal, may increase progressively across more than one, or all, of the bands.

In some embodiments, a third parameter of the audio and/or haptic signal may also be varied in relation to the marker proximity value. Suitably, the first parameter may be the pulse duty (i.e. duty cycle) or beat length as described above, while the third parameter may be the pulse frequency of the audio and/or haptic signal, or vice versa. In some embodiments, the third parameter may be varied continuously in relation to the marker proximity value within at least one band. Suitably, the third parameter may increase with increased proximity to the marker. In some embodiments, the third parameter may be configured to remain substantially constant with respect to the marker proximity value within at least one band. The third parameter may be varied continuously or discontinuously at at least one boundary between two adjacent bands of the plurality of bands. In some embodiments, within at least one band, the pulse length and pulse frequency of the audio and/or haptic signal may both remain substantially constant with proximity to the marker, while varying discontinuously at least at one boundary between the at least one band and an adjacent band. In some embodiments, within at least one band, the pulse duty cycle of the audio and/or haptic signal may remain substantially constant with proximity to the marker, while the pulse frequency increases progressively with proximity to the marker and varies continuously at least at one boundary between the at least one band and an adjacent band. It will be understood that in order to maintain a constant duty cycle with increasing pulse frequency, the pulse length of the signal must decrease within the at least one band.

In some embodiments, the third parameter, e.g. pulse frequency of an audio and/or haptic signal, may increase progressively across more than one band, varying continuously or discontinuously at each boundary between the more than one bands. Within a band of proximity values which is proximal to or at the lower end of the range of proximity values, the pulse frequency may become so fast that the human ear is only able to perceive a continuous tone. In such a proximal band, in some embodiments, the audio signal may in fact be continuous, i.e. not pulsed.

Where a parameter of the audio and/or haptic signal such, for example, as pulse frequency varies within a band, it may vary linearly or non-linearly. In some embodiments, beat frequency may increase non-linearly with proximity to the marker within at least one band. In particular, the pulse frequency may increase with proximity to the marker within each band at an increasing or decreasing rate. Thus, the rate of change of the audio and/or haptic parameter may increase or decrease within at least one band. Suitably, the pulse frequency may increase progressively across two or more contiguous bands at an increasing or decreasing rate, with a continuous change in pulse frequency at each boundary. It has been found that in some embodiments, a decreasing rate of change with proximity to the marker may be advantageous in allowing a user to appreciate better the changes by adding a rhythmic emphasis.

In accordance with the disclosure, the range of the marker proximity value is divided into a plurality of contiguous distance bands. In some embodiments, the plurality of bands may include between about 2 and about 8 bands. In other embodiments there may be a greater number of bands; for example more than about 10 or about 20 bands. In some embodiments, the range of the marker proximity value may be divided into a large number of distance bands; e.g. up to about 100 or more bands.

At least one boundary between two adjacent bands, i.e. the marker position value at the at least one boundary, may be user-defined.

The audio and/or haptic signal may include an audio and/or haptic alert at one or more boundaries between two adjacent bands.

The method may further include generating, by the processor and for output by a display, a graphical interface based on the marker proximity value; and outputting, by the display, the generated graphical interface. A parameter of at least one element of the graphical interface may be varied discontinuously at a boundary between two adjacent bands of the plurality of bands.

For each of the plurality of bands, the at least one parameter of the graphical interface element may be configured to (a) vary linearly with a change in the marker proximity value within the band, (b) vary non-linearly with a change in the marker proximity value within the band, or (c) remain constant with a change in the marker proximity value within the band.

In some embodiments, the rate of change of the at least one parameter of the graphical interface element with marker proximity value may vary discontinuously at the at least one boundary, while the at least one parameter may itself vary continuously across the at least one boundary.

The parameter may be at least one of a colour, transparency, size or position of the element of the graphical interface.

The position of at least one boundary between two adjacent bands, i.e. the marker position value at the at least one boundary, may be user-defined and this position may be represented by a selectable element of the graphical interface.

For at least a first band, a parameter of a first element of the graphical interface may be varied continuously with a change in the marker proximity value within the band. For at least a second band different from the first band, a parameter of a second element of the graphical interface may be varied continuously with a change in the marker proximity value within the band.

At least one element of the graphical interface may include a representation of a probe and its proximity to a marker.

According to a second aspect of the present disclosure there is provided a computer-readable medium comprising instructions which, when executed by a processor, cause the processor to perform the method of the first aspect.

According to a third aspect of the present disclosure there is provided a system, i.e. apparatus, for detecting a marker in a body, including a probe. The probe may comprise a sensor, wherein the sensor is adapted to sense a marker signal emitted by a marker, a property of the signal being indicative of the distance between the marker and the probe. The probe may be configured to generate an input signal in response to the marker signal. The system may further comprise a base station comprising one or more processors and a memory. The memory of the base station may be configured to store computer-readable instructions which, when executed by the one or more processors, cause the base station to perform the method of the first aspect of the present disclosure.

In some embodiments, the system, e.g. the base station, may further comprise at least one user interface device. The user interface device may be selectively operable to generate a sensible signal, i.e. a signal which is susceptible of being perceived by a user by sight, sound or touch. In some embodiments, the base station may comprise a speaker which is arranged to receive the generated feedback signal and to output the signal in audible form. In some embodiments, the base station may include a display for a graphical interface of the kind described above. In some embodiments, the probe may include a haptic actuator. In some embodiments, the system may comprise a further unit comprising a haptic device, which is configured to be worn in close proximity to or in contact with the user's skin for transmitting a generated haptic signal to the user's skin.

According to a fourth aspect of the present disclosure, there is provided a computer-implemented method of detecting a marker in a body. The method comprises receiving, by a processor, an input signal from a probe, where the input signal is generated by a probe in response to detecting a marker signal from the marker and has at least one parameter (e.g. amplitude) which is indicative of the proximity of the probe to the marker. The method may further comprise calculating, by the processor, a marker proximity value based on the input signal, where the marker proximity value corresponds to the distance between the probe and the marker. The method may further comprise generating by the processor and for output by a user interface device, at least one audio signal on having at least one parameter which is indicative of the marker proximity value. The method may further comprises receiving, by the processor, a range of the marker proximity values which is divided into a plurality of predetermined distance bands. The method may further comprise adjusting the generated signal such that at least one parameter of the audio signal selected from pulse length, pulse duty, pulse frequency and rate of change of pitch of the audio signal is varied discontinuously at at least one boundary between two adjacent bands of the plurality of bands. The method may further comprise outputting, by the user interface device, the generated audio signal.

Suitably, the pitch of the audio signal may be increased continuously with proximity to the marker within at least one band and across the boundary between the at least one band and an adjacent band of the plurality of bands. The rate of change of the pitch of the audio signal in relation to the marker proximity value may be varied discontinuously at the boundary between the adjacent bands. The pulse frequency of the audio signal may be increased continuously in relation to the marker proximity value within the at least one band. The duty cycle of the audio signal may be held substantially constant within the at least one band. Thus the pulse length of the audio signal may be varied continuously in relation to the marker proximity value within the at least one band.

Although, the disclosure relates to different aspects and embodiments, it is understood that the different aspects and embodiments disclosed herein can be integrated, combined, or used together as a combination system, or in part, as separate components, devices, and systems, as appropriate. Thus, each embodiment disclosed herein can be incorporated in each of the aspects to varying degrees as appropriate for a given implementation. Further, the various systems, probes, control systems, actuators, transducers, user feedback sources, controllers, components and parts of the foregoing can be used with any suitable diagnostic or surgical guidance system and other methods and conjunction with other devices and systems without limitation.

These and other features of the applicant's teachings are set forth herein.

BRIEF DESCRIPTION OF THE DRAWINGS

For a better understanding of the present invention and to show more clearly how embodiments of it may be carried into effect, reference will now be made by way of example only, to the accompanying drawings, in which:

FIGS. 8A-8E are representations of a graphical user interface according to an embodiment of the disclosure; and FIGS. 9A-9E are representations of a combined audio/visual output according to an embodiment of the disclosure.

DETAILED DESCRIPTION

The present disclosure relates to a detection system, i.e. apparatus, and method for locating the position of an implanted marker in the body, and more particularly to a method of outputting an auditory (or audible), visual, and/or haptic signal and/or combinations of the foregoing of locating the position of the implanted marker. In some embodiments, various signal properties and changes thereto may be monitored and transformed to provide user feedback signals that a user may receive in an efficient manner to avoid sensory overload from excessive data reporting during a demanding diagnostic evaluation or other procedure. Accordingly, unlike various legacy approaches complex data are distilled and presented as actionable user feedback signals that can be used to improve detection outcomes and reduce user fatigue.

The marker may be implanted in a site requiring marking in the body. This may, for example, be a tumour or other lesion or site of interest in soft tissue. Examples include but are not limited to benign lesions, cancerous lesions and lymph nodes.

The marker may be placed in or near a lesion or multiple markers may be placed to mark the margins or perimeter of a surgical site, for example the margins of a soft tissue sarcoma.

Figure 1A:
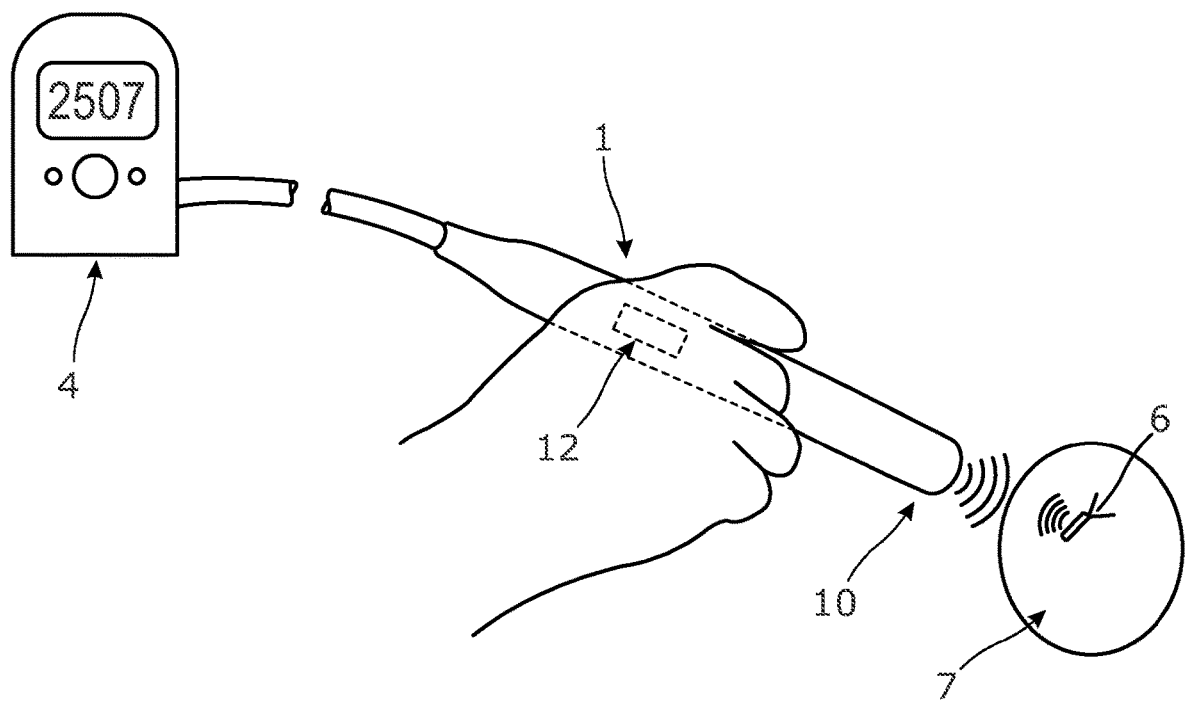
FIG. 1A is a schematic diagram of a magnetic detection system according to an embodiment of the disclosure.

FIG. 1A of the accompanying drawings shows a schematic diagram of a detection system and marker. The detection system 1 comprises a probe or handpiece 10 and a base unit 4. The base unit 4 may include a housing, a power supply, one or more control systems, electronic memory, data storage, one or more processors, one or more microprocessors, one or more application specific integrated circuits (ASICs), a signal processor, a digital signal processor, one or more user input devices such as switch, knob, joystick or touch screen, input signal channel, output signal channel, and other components as disclosed herein. The base unit 4 may include one or more boards and busses such that various components are in electrical or optical communication or combinations thereof with each other. The probe or handpiece 10 is connected to the base unit 4 by any suitable mechanism or signal transmission medium or apparatus (not shown) known to those skilled in the art. For example, the probe or handpiece 10 may be wired to the base unit 4 or may be connected wirelessly to the base unit 4. The probe 10 is operable to detect a signal emitted by a marker 6. The marker 6 may be located within the limits of a surgical site 7.

In an example, the probe 10 is operable to generate a signal or field that excites the marker 6. For example, the probe may generate and detect alternating magnetic fields using for example AC susceptometry, where the marker comprises a magnetic material, e.g., a high susceptibility material.

Alternatively, the detection system may use any other active detection technology, for example, generation and detection of DC magnetic fields using for example DC susceptometry where the marker comprises a magnetic material; generation and detection of induced eddy currents where the marker comprises a conductive material; excitation and or detection using radio-frequency waves or radar waves or other electromagnetic waves or signals where the marker, for example, reflects or absorbs electromagnetic waves; or infra-red radiation excitation and detection where the marker, for example, reflects or absorbs infra-red radiation.

The probe or handpiece 10 of the detection system further contains one or more sensors arranged to detect the signal from the marker 6. The probe 10 generates an input signal and sends the input signal to the base station 4. The input signal is indicative of the distance between the probe 10 and the marker 6. For example, an amplitude of the input signal may correspond to the strength of a response detected from the marker 6.

Figure 1B:
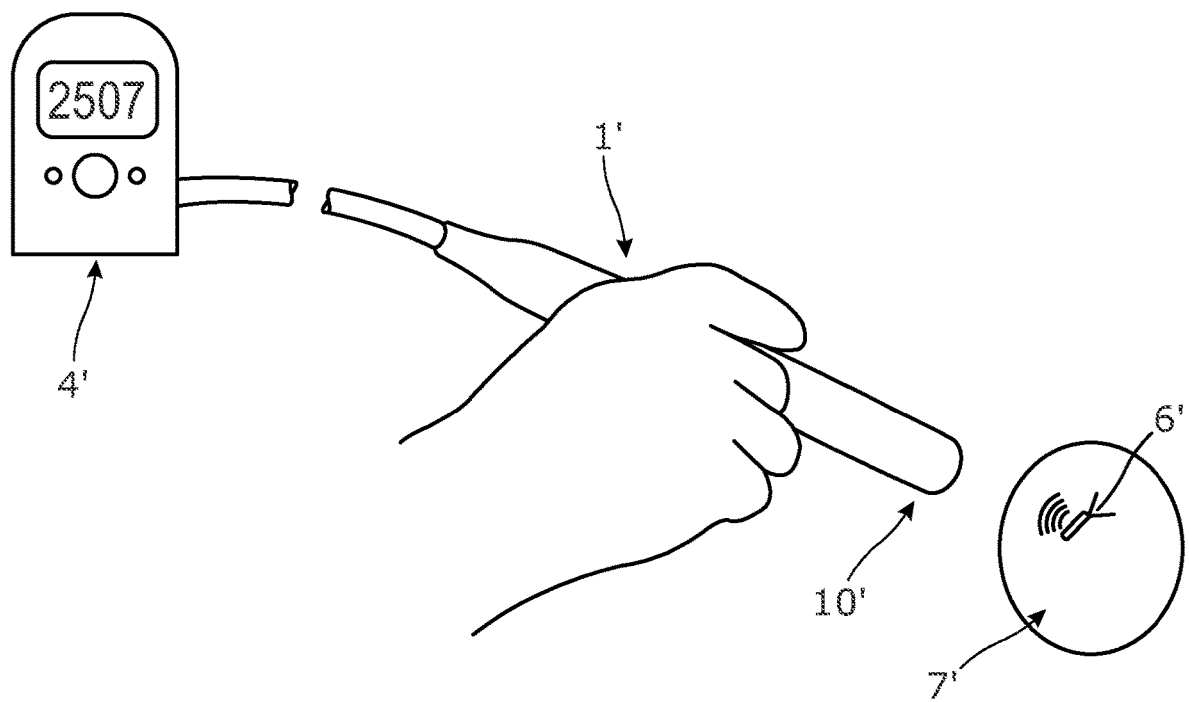
FIG. 1B is a schematic diagram of a magnetic detection system according to an embodiment of the disclosure.

In some implementations, as shown in FIG. 1B, the detection system may use one or more passive detection technologies, where the probe 10' does not generate any signal that excites the marker 6' and detects a signal generated by the marker 6'. For example, the probe 10' may detect radiation or gamma rays, where the marker comprises a radiation emitting substance, e.g., a radioisotope; may detect DC magnetic fields where the marker comprises a magnet or magnetised material; or may detect a radio-frequency identification (RFID) tag where the marker comprises an RFID tag or marker.

In some implementations, the probe 10; 10' may include a haptic actuator 12 which is configured to produce a perceptible haptic signal in a region of the probe where it is usually held by a user in use, as indicated in FIG. 1A.

The base station 4; 4' is operable to generate a user output based on the output signal. A user display and sound generator provided in the base station 4; 4' provide a visual and audio output to the user indicating, for example, the proximity of the marker or the magnitude of the detected signal. The user output may be indicative of the distance between the probe 10; 10' and the marker 6; 6'. The system may indicate the proximity, size, distance, direction or orientation of the marker 6; 6', or combinations of these. In some embodiments, the base station 4; 4' may provide only an audio output indicating the proximity of the marker or the magnitude of the detected signal.

In this implementation, the user output shows an amplitude value of the input signal. The displayed amplitude value increases as the probe 10; 10' is moved closer to the marker 6; 6', thus indicating the proximity of the marker. The base station 4; 4' in this implementation may be configured to output a distance in millimetres (as shown, for example, in FIGS. 8A-E and FIGS. 9A-E below) or any other suitable unit of measurement, corresponding to the distance between the probe 10; 10' and the marker 6; 6'. The base station 4; 4' may be configured to determine a marker proximity value based on the input signal received from the probe 10; 10' e.g. based on the amplitude of the input signal. The marker proximity value corresponds to a distance between the probe 10; 10' and the marker 6; 6'. The base station 4; 4' may be configured to output a distance corresponding to the marker proximity value.

To detect a marker 6; 6' in a typical lesion or site of interest the probe may be configured to have a detection depth of at least about 30 mm, preferably more than 40 mm and more preferably more than about 50 mm. In some examples, the probe 10; 10' may be configured to give the same magnitude of response regardless of the direction in which the marker is approached. In this way, the detection system can provide consistent feedback on the location of the marker relative to the probe.

In the implementation shown in FIG. 1A, the marker 6 comprises at least one piece of magnetically responsive material and may have a non-linear magnetic susceptibility. In some implementations, a magnetisation of the material may respond in a non-linear fashion to an external magnetic field, such that a reversal of magnetisation generates a magnetic pulse with rich harmonic components.

The probe 10 of the detection system further contains one or more sense coils arranged to detect the changes in the magnetic field caused by the change in magnetisation of the marker 6. The probe 10 generates an input signal and sends the input signal to the base station 4. The input signal is indicative of the distance between the probe 10 and the marker 6. For example, an amplitude of the input signal may correspond to the strength of a response magnetic field detected from the marker 6.

In both cases, the base station 4; 4' generates a user output based on the output signal. A user display and sound generator provided in the base station 4; 4' provides a visual and audio output to the user indicating, for example, the proximity of the marker or the magnitude of the magnetic signal. The user output is indicative of the distance between the probe 10; 10' and the marker 6; 6'. The system may indicate the proximity, size, distance/direction or orientation of the marker 6; 6', or combinations of these.

To detect a marker 6; 6' in a typical lesion or site of interest the probe may be configured to have a detection depth of at least about 30 mm, preferably more than about 40 mm and more preferably more than about 50 mm. In some examples, the probe may be configured to give the same magnitude of response regardless of the direction in which the marker is approached. This is to provide consistent feedback to a surgeon on the location of the marker relative to the probe.

In other cases, the magnetic detection system 10; 10' may provide a more accurate indication of the size of a magnetic marker, where the magnetic marker 6; 6' may correspond to a sample of any material providing a non-linear magnetic response. That is, by determining a marker proximity value corresponding to a distance between the probe and a closest point of the marker, then the marker proximity value may be used to map a volumetric extent of the marker 6; 6'.

Figure 2:
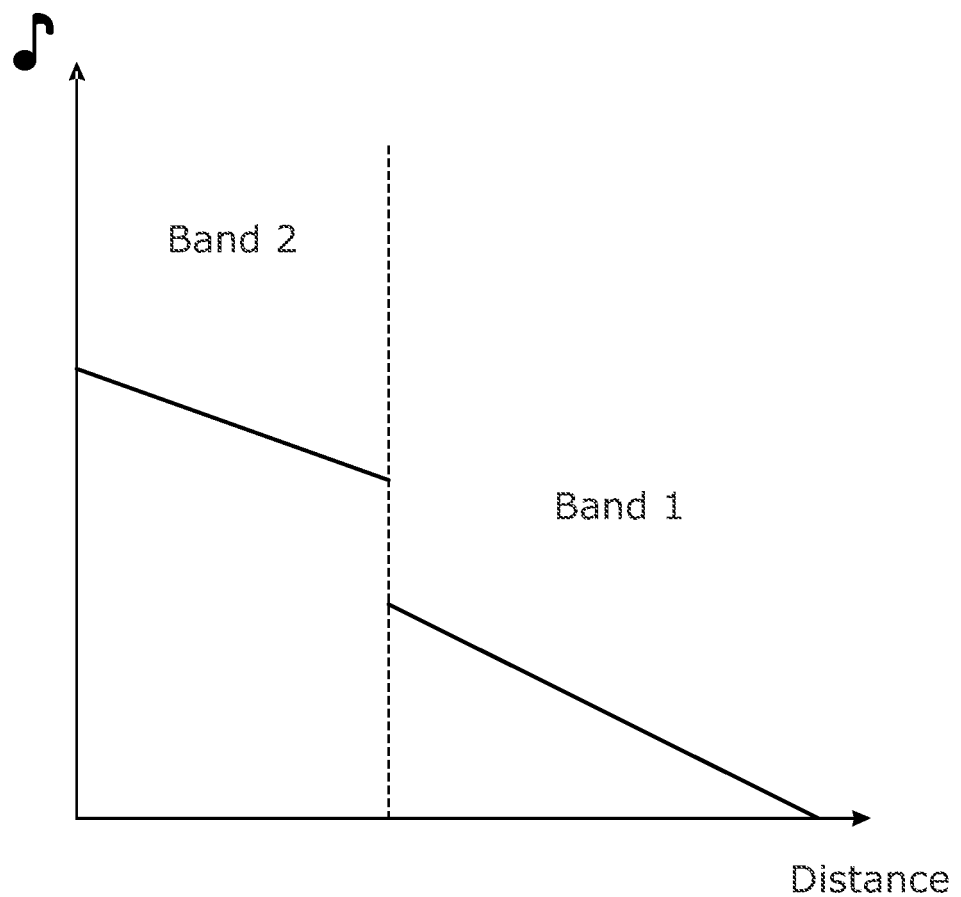
FIG. 2 is a representation of a user feedback signal, for example an audio signal, according to an embodiment of the disclosure.

FIG. 2 shows a representation of a user feedback signal, for example an audio or haptic signal, to be output by the base station 4; 4', according to an embodiment. The x-axis represents the distance between the probe 10; 10' and the marker 6; 6', which may correspond to a determined marker proximity value. The y-axis represents a parameter of the user feedback signal. The parameter may be any suitable parameter or combination of parameters of the feedback signal. For example, according to the type of feedback signal, the parameter may be any of an amplitude (volume), loudness, tone, pitch, timbre, pulse (beat) frequency or pulse (beat) pattern of the signal. As discussed below, the pulse pattern may occur in the length (duration) of each individual pulse and/or in the pulse duty.

In the case of an audio signal, amplitude is the acoustic or electrical level of the audio signal waveform signal level, also referred to as the volume. Loudness is the perceived volume of an audio signal. For a haptic signal, amplitude is the physical strength or electrical level of the haptic signal waveform signal level. A tone is a sound that can be recognized by its regularity of vibration or frequency. A simple tone has only one frequency, although its intensity may vary. Pitch is defined as the audio frequency of a sound, and often refers to the fundamental frequency of a complex sound. Timbre is the tonal 'colour' of a sound, also described as the unique quality or characteristic sound of a musical instrument or sound source. Timbre is what makes a particular sound different from another, even when they have the same pitch and loudness. Timbre includes the harmonic content of a sound, its dynamic characteristics such as vibrato, and the attack-decay envelope of the sound. Pulse (beat) frequency here is defined as the number of pulses (beats) per unit time, where the sound is in the form of repeated pulses (beats) or repeated sounds, i.e. a series of discreet pulses. Pulse (beat) pattern refers to the variation over time or pattern over time of pulses (beats) or repeated sounds or vibrations within an audio or haptic signal. It may for example include variation of any of pulse (beat) length or pulse duty, mark-space ratio, timing or rhythm.

In FIG. 2, the distance range is divided into two bands, labelled Band 1 and Band 2. Band 1 corresponds to a part of the distance range which is greater (i.e. further from the marker) than that of Band 2. That is, Band 2 corresponds to a closer proximity between the probe 10; 10' and the marker 6; 6'. Within Band 1, the feedback (e.g. haptic or audio) signal is configured to vary continuously with a change in distance between the probe 10; 10' and the marker 6; 6'. The parameter of the signal is configured to increase linearly with increasing proximity. For example, a pitch and/or volume of an audio signal may rise as the probe 10; 10' is moved closer to the marker 6; 6'.

Within Band 2, the feedback (e.g. haptic or audio) signal is also configured to vary continuously with a change in distance between the probe 10; 10' and the marker 6; 6'. The parameter of the signal is configured to increase linearly with increasing proximity. For example, a pitch and/or volume of an audio signal may rise as the probe 10; 10' is moved closer to the marker 6; 6'. The parameter is configured to vary at a lower rate in Band 2 than in Band 1. In some embodiments, the parameter may vary at a higher rate or the same rate in Band 2 as in Band 1. In some examples, the parameter may not change with varying distance across one or more of the bands.

At the boundary between Band 1 and Band 2, depicted by a vertical dotted line, there is a discontinuity or disjoint in the value of the parameter of the feedback (e.g. audio or haptic) signal. There is a step change in the parameter when moving from Band 1 to Band 2. In some embodiments, the change is an increase. For example, there may be a step increase in the pitch and/or volume of an audio signal, in particular a clearly audible jump in pitch and/or volume, as the probe 10; 10' is moved closer to the marker 6; 6'.

In this way, the user of the system 10; 10', e.g., a surgeon, can be provided with a clear audio or haptic indication of the boundary between Band 1 and Band 2. The boundary between bands may correspond to a fixed distance between the probe 10; 10' and the marker 6; 6'. In this way, the user may be provided with a clear indication of the fixed distance. For example, the boundary between Band 1 and Band 2 may be set at 10 mm, so the user receives a clear indication of whether the proximity between the probe 10; 10' and the marker 6; 6' is greater or less than about 10 mm. In some examples, the boundary position may be pre-set, or may be set by a user. In some embodiments, by using known separation distances, a user can make decisions when demarking regions of interest by writing on a tissue region or providing a legend or reference marks when photographing tissue as part of a preparations for a procedure.

The boundary position may be set at a distance corresponding to the size of a tumour or lesion to be removed during a procedure, thus providing a surgeon with a clear indication of the extent of the tissue to be excised. In this way, a more accurate guide to the extent of tissue to be excised can be provided, reducing the risks of (a) incomplete removal of the tumour or lesion, and (b) excessive tissue removal. By providing a clear audio and/or haptic signature, such an indication can be provided without diverting the attention or gaze of the surgeon, thus reducing time taken to detect the marker, and reducing the occurrence of unintended hand movements. The speed and accuracy of the procedure can therefore be improved, and the system can further reduce the risks of (a) incomplete removal of the tumour or lesion, and (b) excessive tissue removal.

Figure 3A:
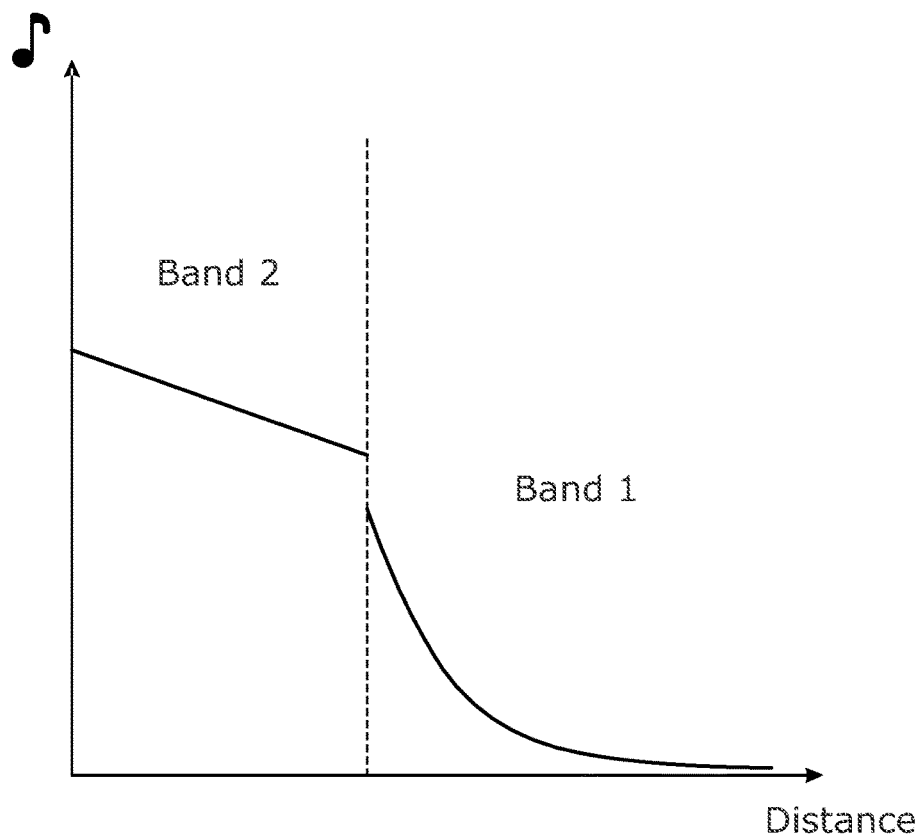
FIGS. 3A and 3B are representations of user feedback signals, for example audio signals, according to embodiments of the disclosure.

FIG. 3A shows a representation of a feedback (e.g. audio or haptic) signal to be output by the base station 4; 4', according to a different embodiment. As shown, the parameter of the signal is configured to vary non-linearly with a change in distance across Band 1. That is, the parameter is configured to change with a changing rate as the proximity between the probe 10; 10' and the marker 6; 6' increases. In some embodiments, the parameter is configured to increase with an increasing rate as the proximity between the probe 10; 10' and the marker 6; 6' increases. Alternatively, the parameter may be configured to increase with a decreasing rate as the proximity increases. The signal in Band 2 is substantially as described with respect to FIG. 2. As described with respect to FIG. 2, there is a discontinuity, suitably a clearly distinct discontinuity, in the value of the audio or haptic parameter at the boundary between Band 1 and Band 2. The various boundaries at which a discontinuity may occur are shown by dotted lines in various embodiments.

Figure 3B:
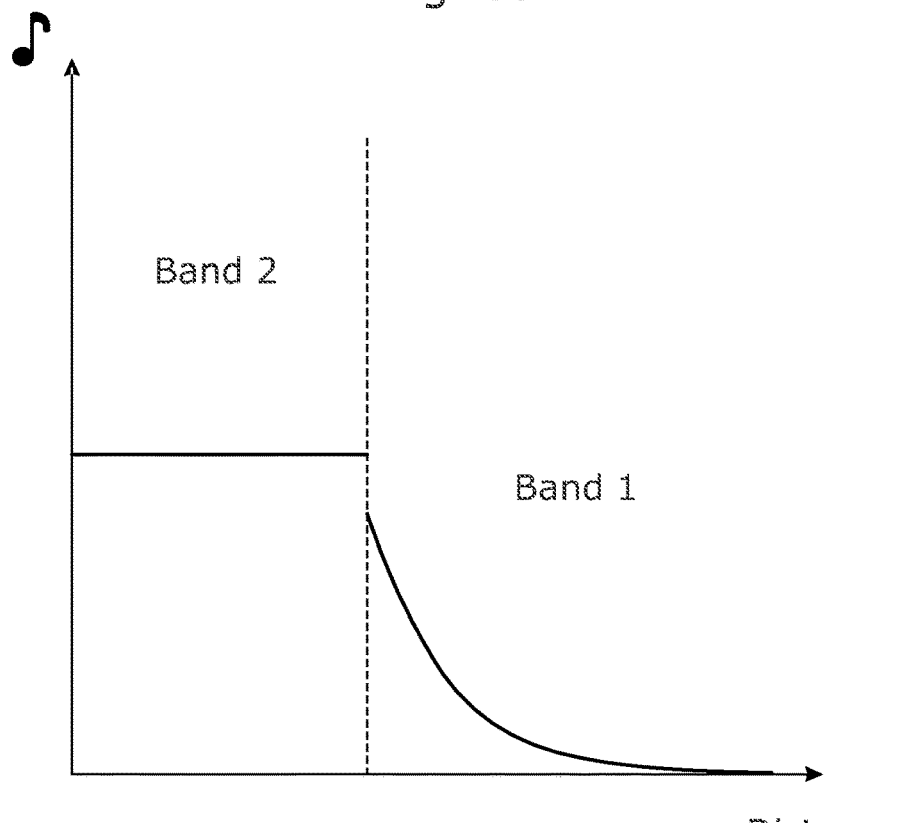

FIG. 3B shows a representation of a feedback (e.g. audio or haptic) signal to be output by the base station 4; 4', according to a yet another embodiment. As shown, the parameter of the signal is configured to vary non-linearly with a change in distance across Band 1, substantially as described with respect to FIG. 3A. The parameter of the signal in Band 2 is configured to remain constant with a change in distance across Band 2. That is, the parameter, e.g., a pitch or volume or another parameter of an audio signal, does not change as the probe 10; 10' moves closer to the marker 6; 6'. As described with respect to FIG. 2, there is a discontinuity, namely a clearly discernible discontinuity, in the value of the audio or haptic parameter at the boundary between Band 1 and Band 2.

Figure 4A:
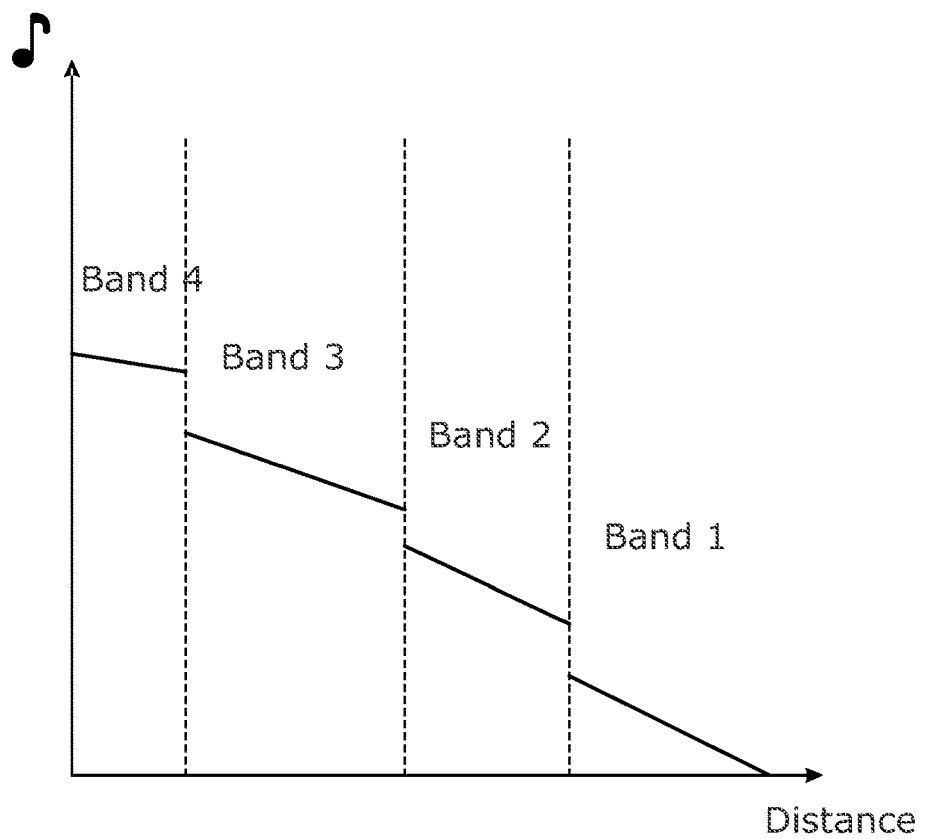
FIGS. 4A to 4D are representations of feedback signals, for example audio signals, according to embodiments of the disclosure.

FIG. 4A shows a representation of a feedback (e.g. audio or haptic) signal to be output by the base station 4, according to a yet another embodiment. The distance range is divided into four bands, labelled as Bands 1 to 4, respectively. Band 1 corresponds to a part of the distance range which is greatest, and Band 4 corresponds to a closest proximity between the probe 10; 10' and the marker 6; 6'. Within each band, the signal is configured to vary continuously with a change in distance between the probe 10; 10' and the marker 6; 6'. In some embodiments, the parameter of the signal, e.g. pitch and/or volume of an audio signal, is configured to increase continuously with increasing proximity across each of the bands. The parameter is configured to increase at a different rate for each of the four bands. The rate of change for each band may be pre-set, or may be selected by a user.

As shown by the dotted lines, there are three boundaries between adjacent bands. At each of the boundaries there is a discontinuity in the value of the audio or haptic parameter. At each of the boundaries there is a step change in the value of the audio or haptic parameter as the probe 10; 10' moves closer to the marker 6; 6'. In some embodiments, one or more of the boundaries may be configured with a step increase or a step decrease in the value of the audio or haptic parameter. Alternatively, the audio or haptic parameter may vary continuously across one or more of the boundaries, i.e., there may be no step change at one or more of the boundaries. Other parameters of the audio or haptic signal may vary continuously across one or more of the boundaries, remain constant, or also have a step change in value.

Figure 4B:
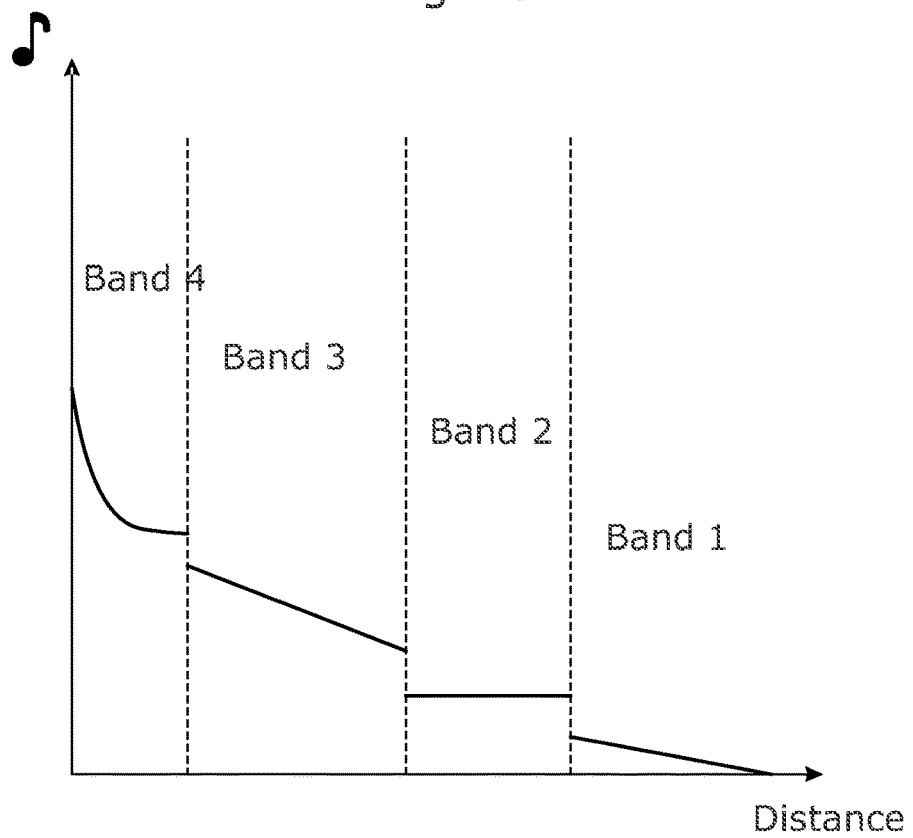

FIG. 4B shows a representation of a feedback (e.g. audio or haptic) signal to be output by the base station 4; 4', according to a yet another embodiment. As shown, the parameter of the signal in Band 2, e.g. volume and/or pitch for an audio signal, is configured to remain constant with a change in distance across Band 2, substantially as described with respect to Band 2 in FIG. 3B. The parameter of the audio or haptic signal is configured to vary non-linearly with a change in distance across Band 4, substantially as described with respect to Band 1 in FIG. 3A. The signals in Bands 1 and 3 are substantially as described with respect to FIG. 4A. As described with respect to FIG. 4A, there is a discontinuity in the value of the audio or haptic parameter at each of the boundaries between adjacent bands.

Figure 4C:
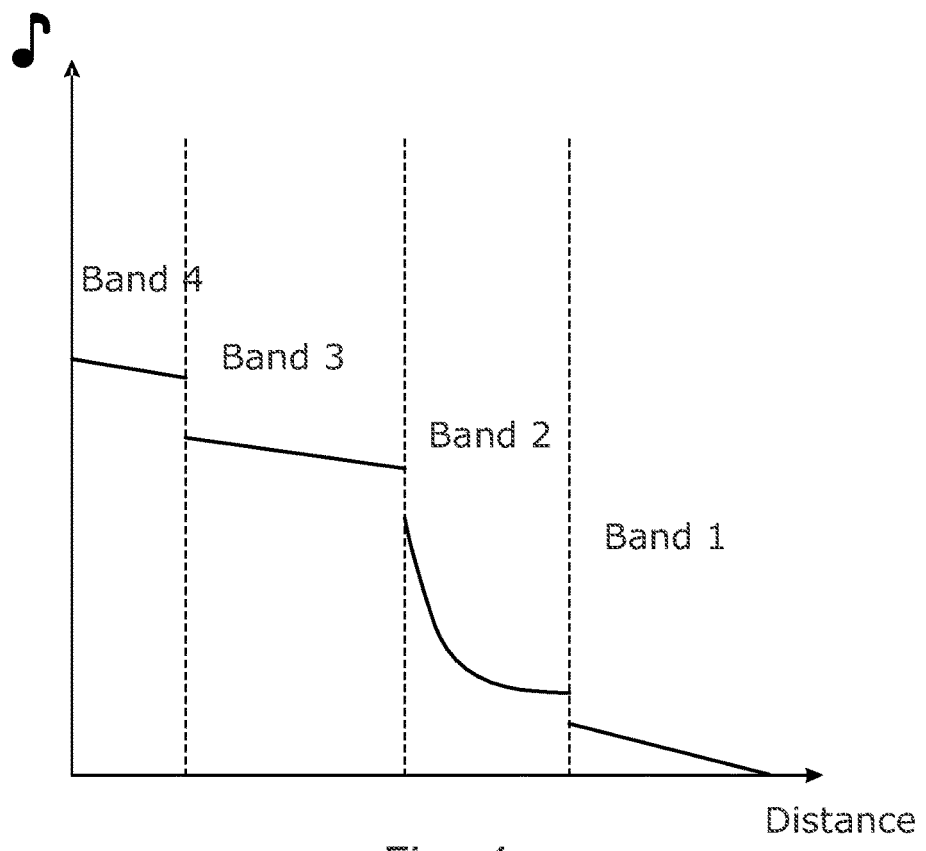

FIG. 4C shows a representation of a feedback (e.g. audio or haptic) signal to be output by the base station 4; 4', according to still another embodiment. In this embodiment, the parameter of the signal, e.g. volume and/or pitch for an audio signal, is configured to vary linearly at the same rate across each of Bands 1, 3 and 4. The signal is configured to vary non-linearly across Band 2. As described with respect to FIG. 4A, there is a discontinuity in the value of the parameter at each of the boundaries between adjacent bands.

Figure 4D:
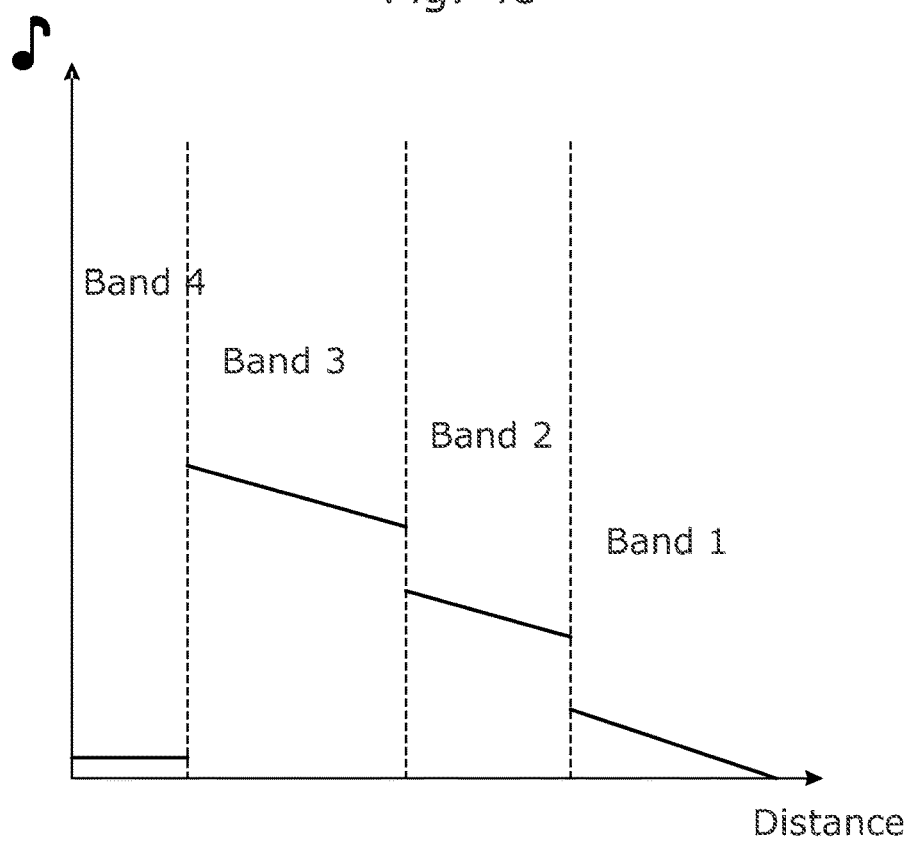

FIG. 4D shows a representation of a feedback (e.g. audio or haptic) signal to be output by the base station 4; 4', according to still yet another embodiment. Bands 1 to 3 are substantially as described with respect to FIG. 4A. The parameter of the signal in Band 4, e.g. volume and/or pitch for an audio signal, is configured to remain constant with a change in distance across Band 4. The fixed value of the parameter is Band 4 is significantly lower than the value of the parameter in Band 3. That is, there is a large step decrease in the value of the audio or haptic parameter at the boundary between Band 3 and Band 4. In an example, as the probe 10; 10' is moved closer to the marker 6; 6', the pitch of an audio signal may rise across Bands 1 to 3 before sharply falling to an unchanging low pitch in Band 4. In this way, the signal may provide the user with an indication of increasing proximity, as a clear warning with the probe 10; 10' is too close to the marker 6; 6'.

Figure 5A:
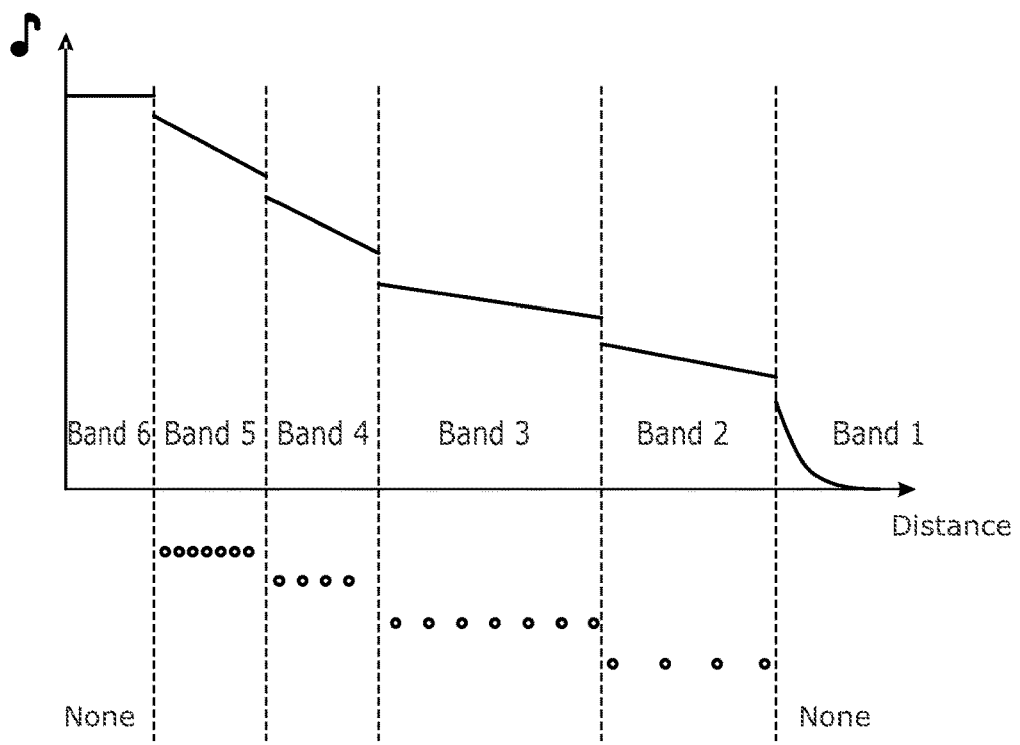
FIGS. 5A to 5C are representations of audio signals according to embodiments of the disclosure.

FIG. 5A shows a representation of an audio signal to be output by the base station 4; 4', according to yet another embodiment. The distance range is divided into six bands, labelled as Bands 1 to 6, respectively. Embodiments may have any number of bands from 2 to 6 and, in some examples may have up to 8 or more bands. As shown, two or more parameters of the audio signal may be varied with a change in the marker proximity value.

As shown above in FIG. 5A, a first parameter of the audio signal is varied across Bands 1 to 6, substantially as described above. The first parameter may be, for example, a tone and/or pitch and/or volume of the audio signal. The first parameter is configured to increase non-linearly across Band 1, to increase linearly across Bands 2 to 5, and to remain constant across Band 6. As shown below in FIG. 5A, a second parameter of the audio signal may also be varied across Bands 1 to 6. According to the present embodiment, the second parameter of the audio signal may be, for example, a beat frequency of the audio signal. The figure represents a beat frequency (number of beats per minute) by the spacing of the dots, with widely spaced dots (e.g., Band 2) representing a lower frequency than more closely spaced dots (e.g., Band 5).

In each of Bands 2 to 5 the beat frequency is constant within the band. The beat frequency increases with each band from 2 to 5. In each of Bands 1 and 5 there is no beat frequency ("none") and a constant tone is emitted. At each of the boundaries between bands, there is a discontinuity in the second parameter of the audio signal. At each boundary, there is a step change in the value of the beat frequency, which is suitably clearly discernible to a user.

Figure 5B:
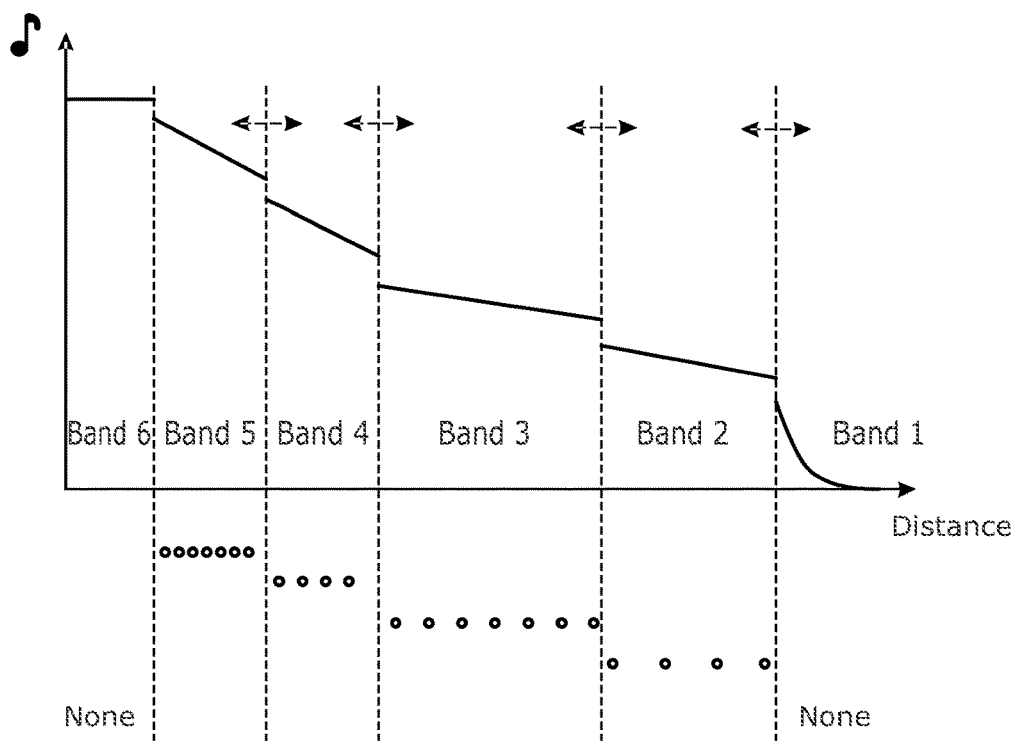

In some embodiments, as indicated by double-headed arrows in FIG. 5B, the position of one or more of the boundaries between adjacent bands can be adjusted. The position of each boundary may be pre-set for example according to bands of distance between probe and marker, or may be set by a user, e.g., via a user interface. It will be understood that any of the embodiments described herein may be adapted such that the boundaries may be adjusted in this way.

In some examples, the overall range of pitch (fundamental frequency) used across all the bands may suitably be limited to be within the audible frequency range for the human ear. For example, the range may be between 20 Hz and 20 kHz, and may suitably be between 100 Hz and 15 kHz. In some examples, the range of pitch may be limited to be within a range that is 'comfortable' to listen to i.e. lower than approximately 3000 Hz, and may be less than 2000 Hz. In some examples, a range of pitches may be between about 200 Hz and about 3000 Hz and, in some examples, may be between about 200 Hz and about 2000 Hz.

Figure 5C:
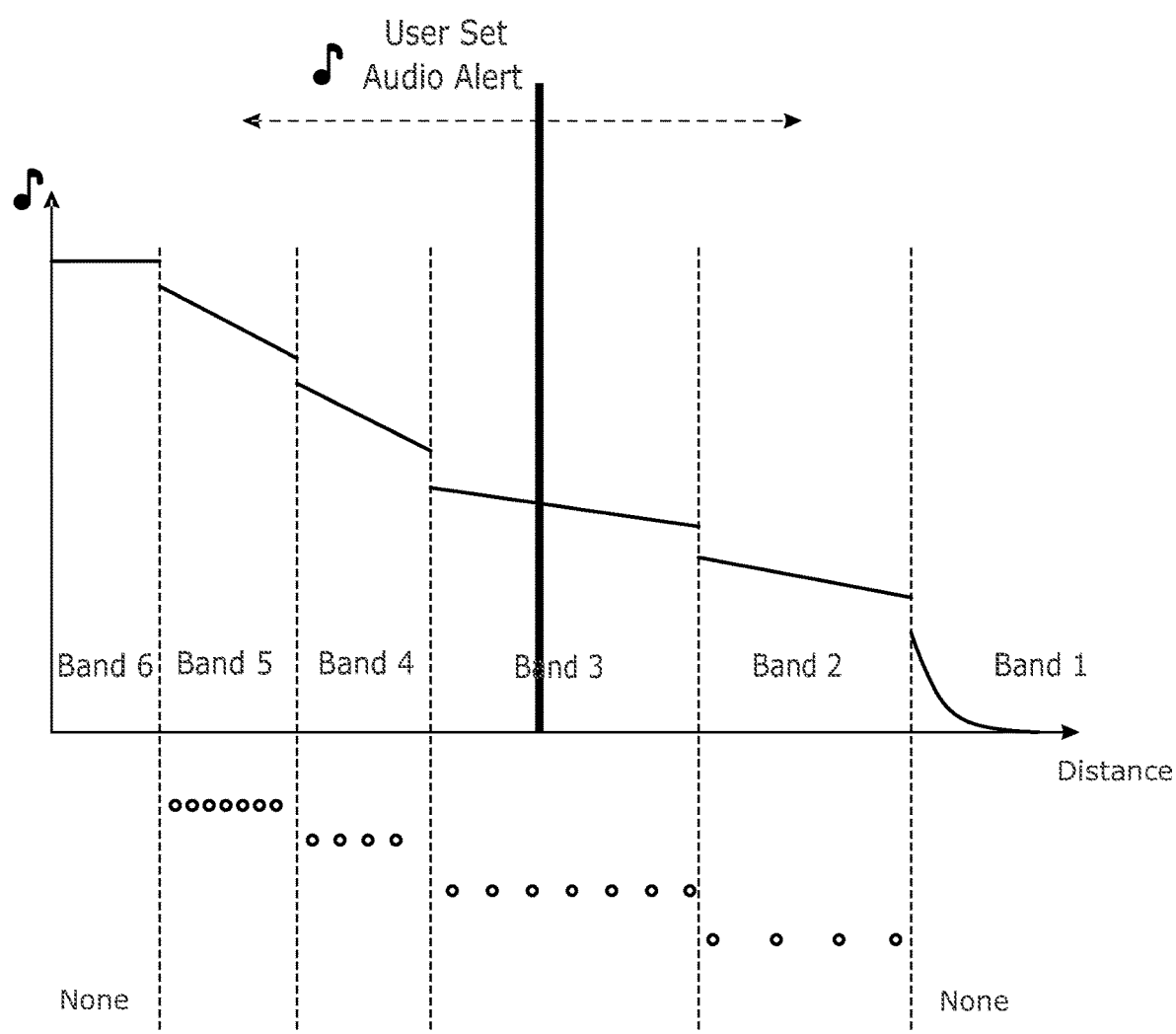

As shown in FIG. 5C, the audio signal may further comprise one or more audio alerts. The or each audio alert suitably comprises an individual audio signature output at a predetermined point on the distance range. In some embodiments, the audio alert is unidirectional, such that the alert in output only when the predetermined point is passed in a certain direction. For example, the base station 4; 4' may be configured to output the audio alert only if the probe 10; 10' passes the predetermined point as it is moving closer to the marker 6; 6'. Alternatively, the audio alert may be bidirectional, and the alert may be output when the predetermined point is passed in either the increasing or decreasing signal direction.

The position of the audio alert may be preset, or may be set by a user, e.g., via a user interface. In some embodiments, the user may add or remove one or more audio alerts from the audio signal. In some embodiments, audio and/or haptic alerts may be positioned at one or more of the boundaries between adjacent bands. Alternatively, audio and/or haptic alerts may be positioned at any point within any band. Audio and/or haptic alerts within a band may be considered as being positioned on a boundary between two similar bands with no discontinuity in any audio and/or haptic signal parameter. For example, in FIG. 5C, Band 3 may be considered as two bands having the same linear rate of change in the first parameter and the same constant value for the second parameter.

As described above in relation to FIGS. 5A, 5B and 5C, in some implementations, two or more parameters of an audio signal may vary according to the proximity of the probe to the marker. For example, as described, the pitch of the audio signal may vary as between two or more bands, and the audio signal may be modulated in at least one band to provide a stream of audible beats, with the frequency and/or length of the beats varying between adjacent bands. It has been found that some users may gain a better intuition for the distance of the probe from the marker when the pitch changes continuously across at least two adjacent bands without any step change at the boundary between the bands, while the change in length of the beats is discontinuous as between the two adjacent bands. That is to say, the change in pitch of the audio signal across the boundary between the at least two bands may be continuous, while the change in length of the beats may be discontinuous at the boundary. In at least one band, the audio signal may be unmodulated so it does not beat. Suitably, the pitch of the audio signal may vary continuously within each band, and as disclosed herein, in some implementations, the rate of change of the pitch of the audio signal may change discontinuously at a boundary between at least two bands, e.g. when the rate of change of pitch with marker proximity value is different as between the two bands. Suitably, the frequency of the beats may vary continuously within the at least one band. In some embodiments, the length or duty cycle of the beats may be substantially constant within the band, while the frequency of the beats (i.e. pulse period frequency) increases progressively with increasing proximity to the marker.

Similarly, in some embodiments, two or more parameters of a haptic signal may vary according to the proximity of the probe to the marker. For example, the haptic signal may comprise a stream of perceptible pulses, with the frequency and/or length of the pulses varying between adjacent bands. The amplitude of the haptic signal may vary as between two or more bands.

In some embodiments, an audio signal may be combined with a haptic signal which controls a haptic actuator (not shown) in the probe 1; 1' or another unit in proximity to the user's skin. At least one parameter of each of the audio and haptic signals may vary across the different bands. For example, an audio signal with parameter such, for example as pitch or volume, which varies as between two or more bands may be combined with a haptic signal comprising a stream of pulses, with the frequency and/or length of the pulses varying between adjacent bands. The pitch or volume of the audio signal may change continuously across at least two adjacent bands without any step change at the boundary between the bands, while the change in frequency or length of the haptic pulses may be discontinuous as between the two adjacent bands. That is to say, the change in pitch or volume of the audio signal across the boundary between the at least two bands may be continuous, while the change in frequency or length of the haptic pulses may be discontinuous at the boundary. Suitably, the pitch of the audio signal may vary continuously within each band, and as disclosed herein, in some implementations, the rate of change of the pitch of the audio signal may change discontinuously at a boundary between at least two bands, e.g. when the rate of change of pitch with marker proximity value is different as between the two bands. The frequency of the haptic pulses may vary continuously within each band. In some embodiments, the duty cycle of the pulses may be substantially constant within each band, while the frequency of the pulses (i.e. pulse period frequency) may increase progressively with increasing proximity to the marker.

In some embodiments, at least one parameter of the audio signal and at least one parameter of the audio signal may be synchronised with one another. Thus in some embodiments, the audio signal may be modulated in at least one band to provide a stream of audible beats which are synchronised with corresponding haptic pulses of the haptic signal. For example, in at least one band, the audio and haptic signals may have the same pulse frequency and/or length. In at least one band, the audio signal may be unmodulated, so it does not beat.

Figure 6:
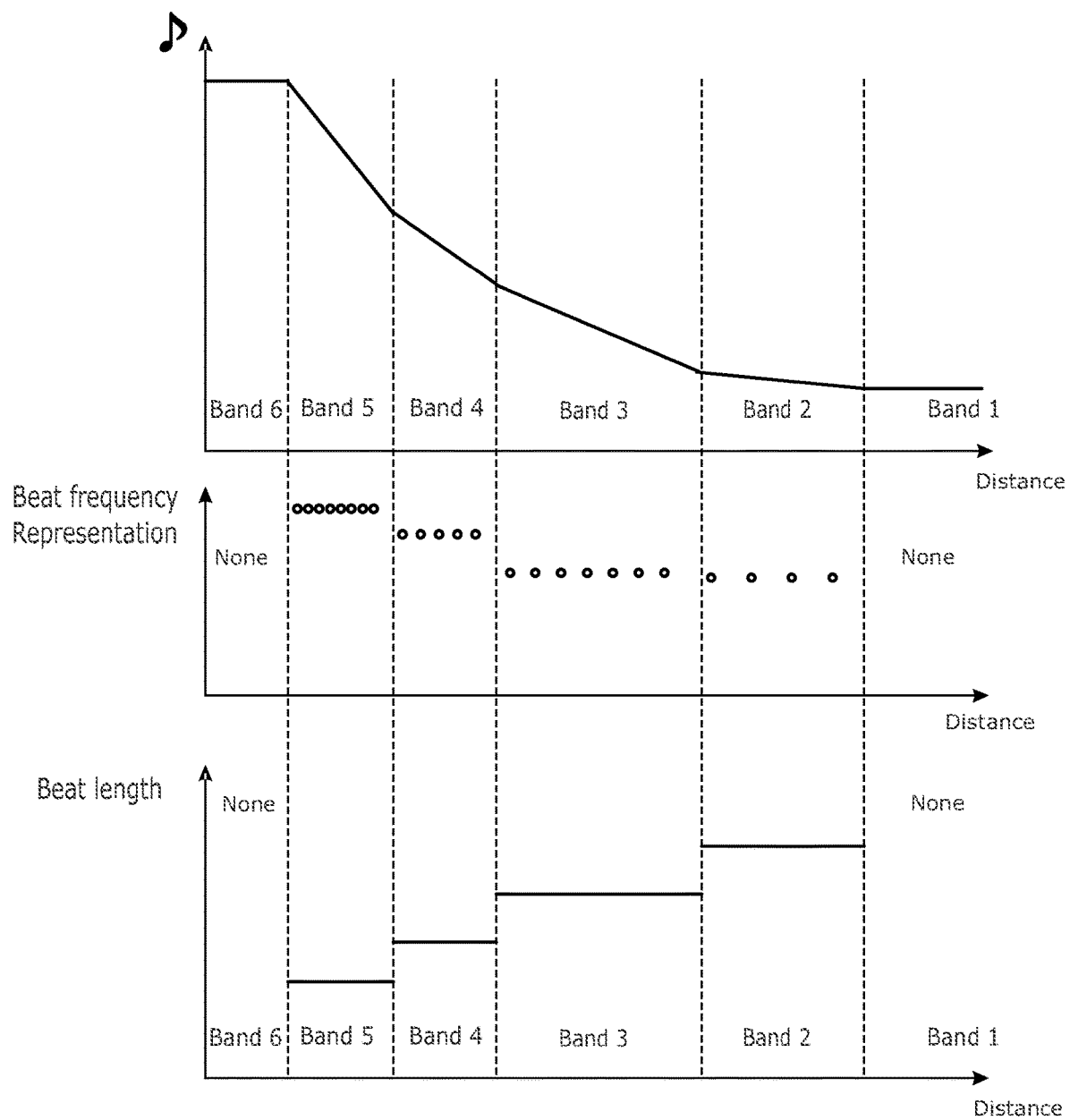
FIG. 6 is a representation of an audio signal according to an embodiment of the disclosure, which comprises a continual series of discreet beats, the beat frequency, beat length and a rate of change of at least one other parameter (e.g. tone or volume) of the audio signal varying discontinuously at boundaries between adjacent bands of a range of marker proximity value, while the at least one other parameter of the audio signal varies continuously across the boundaries.

FIG. 6 illustrates an example in which a first parameter of the audio signal varies continuously at each boundary between a plurality—in this case six—successive bands, while second and third parameters of the audio signal change discontinuously at each boundary. In particular, as shown in an upper section of FIG. 6, the first parameter of the audio signal is varied across Bands 1 to 6. The first parameter may be, for example, a tone, pitch or volume of the audio signal. The first parameter is configured to increase linearly with proximity to the marker 6; 6' across each of Bands 2 to 5, and to remain constant across Bands 1 and 6. It will be noted that while the first parameter of the audio signal varies continuously across the boundaries between adjacent bands, the rate of change of the first parameter with marker proximity value varies discontinuously at each boundary, as described above. In particular, the rate of change of the first parameter increases with each successive band that is closer to the marker 6; 6'. Thus, in some implementations, the rate of increase of the frequency (pitch) of the audio signal may undergo a step change at each boundary.

As shown in the middle section of FIG. 6, the second parameter of the audio signal is varied across Bands 1 to 6. According to this implementation, the second parameter of the audio signal is, by way of example, a beat frequency of the audio signal. The middle section of FIG. 6 thus represents a beat frequency (e.g. number of beats per minute) by the spacing of the dots, with widely spaced dots (e.g., Band 2) representing a lower frequency than more closely spaced dots (e.g., Band 5). In each of Bands 2 to 5, the beat frequency is constant within the band. The beat frequency increases with each band from 2 to 5. In each of Bands 1 and 6 there is no beat frequency ("none") and a constant tone is emitted. In an alternative implementation, the audio signal may still be modulated within Band 1 to produced beats, but the beat frequency may be so fast that it becomes saturated, so that the human ear can only perceive a continuous tone. This may be more convenient to implement from a programming point of view. At each of the boundaries between bands, there is a discontinuity in the second parameter of the audio signal, for example a step change in the value of the beat frequency.

According to the present implementation, the third variable parameter of the signal is, by way of example, a beat length (i.e. beat duty) of the audio signal. The bottom section in FIG. 6 represents a discontinuous beat length variation as between Bands 2 to 5. In each of Bands 2 to 5 the beat length is constant within the band. However, the beat length decreases with each band from 2 to 5. It will be understood that since the beat frequency is constant within each of Bands 2 to 5, the beat duty cycle also decreases with each band from 2 to 5. In each of bands 1 and 6 there is no beat ("none") and a constant tone is emitted.

At each of the boundaries between adjacent bands, there is a discontinuity in the second and third parameters of the audio signal. At each boundary, there is a step change in the value of the beat frequency and beat length. Meanwhile the first parameter changes continuously at each boundary, thereby maximising use of the full range of the first parameter to indicate proximity to the marker across the bands. In a variant, the beat frequency of the audio signal may change continuously across at least two adjacent bands, with no step change at the boundary between the bands.

In another variant, the base station 4; 4' may also generate a haptic signal to control a haptic actuator within the probe 1; 1' or another unit in close proximity to the user's skin. The haptic signal may comprise a series of pulses having a frequency and/or length which matches the second and/or third parameters (beat frequency and/or beat length) of the audio signal in at least one of the bands. Suitably, the frequency of the haptic pulses may be identical to the frequency of the audio beats in at least one band. The middle and/or bottom sections may therefore also represent the second and third parameters of the haptic signal.

In yet another variant, the audio signal may be unmodulated in one or more of the bands, having only a first parameter which varies continuously at each boundary between the bands as described above, while the pulse frequency of the haptic signal changes, e.g. increases, with each band. Suitably, the pulse frequency of the haptic signal may increase with each band from 2 to 5, while in each of Bands 1 and 6 there may be no haptic signal, but other variations will be apparent to those skilled in the art. At each of the boundaries between bands, there may a discontinuity in the frequency and/or length or duty cycle of the haptic signal, for example a step change in the value of the pulse frequency.

Figure 7:
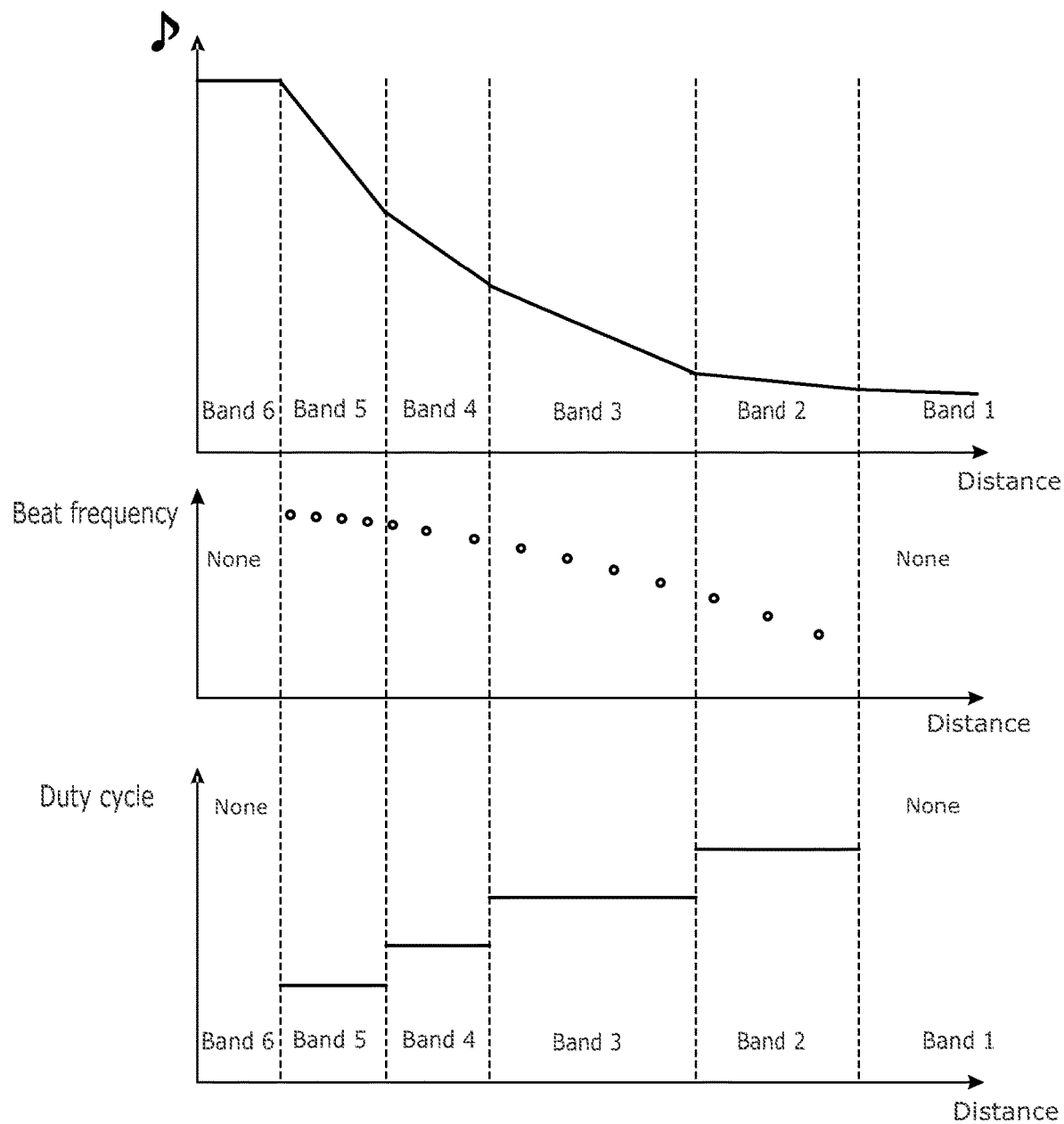
FIG. 7 is a representation of an audio signal according to an embodiment of the disclosure, which comprises a continual series of discreet beats, the duty cycle and rate of change of at least one other parameter (e.g. tone) of the audio signal varying discontinuously at boundaries between adjacent bands of a range of marker proximity value, while the at least one other parameter of the audio signal and the beat frequency vary continuously across the boundaries.

FIG. 7 illustrates yet another example in which first and second parameters of the audio signal vary continuously at each boundary between a plurality—in this case six— successive, contiguous bands, while a third parameter of the audio signal changes discontinuously at each boundary. In particular, as shown in middle and upper sections of FIG. 7, the first and second parameters of the audio signal are varied across Bands 1 to 6.

In the present example, the first parameter is a pitch of the audio signal. The first parameter is configured to increase linearly across each of successive Bands 1 to 5, and to remain substantially constant across Bands 6. It will be noted that while the first parameter of the audio signal varies continuously across the boundaries between adjacent bands, the rate of change of the first parameter with marker proximity value varies discontinuously at each boundary, as described above. In particular, the rate of change of the first parameter increases with each successive band that is closer to the marker. Thus, in some implementations, the rate of increase of the frequency (pitch) of the audio signal may undergo a step change at each boundary. In other implementations, the first parameter may be a volume or another parameter of the audio signal.

The second parameter in the present example is a beat frequency of the audio signal. The second parameter is configured to increase progressively across each of Bands 2 to 5 and continuously across the internal boundaries between Bands 2-5. Thus, the pulse period of the audio signal decreases progressively with proximity across these bands. Further, in the present example, the second parameter increases non-linearly with proximity. More particularly, the rate of increase of beat frequency declines progressively with proximity to a marker. However, it will be understood that in variations of the present example, the second parameter may vary linearly across one or more of the bands, or the rate of change of the second parameter may increase with proximity; the beat frequency may decline with proximity to the marker; and/or the second parameter may change discontinuously at one or more of the boundaries. In the present example, the second parameter remains constant across Band 1, such that the audio signal represents a constant tone (i.e. beat frequency is zero) in Band 1. In Band 6, the audio signal is still modulated to provide a pulse, but the pulse frequency is so high that the audio signal becomes saturated and individual pulses cannot be perceived by the human ear, such that the user hears only a continuous tone. In a variant, the second parameter may remain constant across Band 6, such that, like in Band 1, the audio signal does in fact represent a constant tone in Band 6 too.

Meanwhile, the third variable parameter of the audio signal in the present example is a duty cycle of the audio signal. As will be understood from the bottom section of FIG. 7, the duty cycle is constant within each of Bands 2 to 5, and decreases with each successive band from Band 2 to Band 5, such that the duty cycle undergoes a step change at each internal boundary between Bands 2-5. As noted in the previous paragraph, in each of Bands 1 and 6 there is no beat ("none") and a constant tone is emitted.

At each of the boundaries between adjacent bands, there is a discontinuity in the third parameter of the audio signal. In particular, at each boundary, there is a step change in the value of the pulse length. Meanwhile the first and second parameters change continuously at each boundary, thereby maximising use of the full range of the first and second parameters to indicate proximity to the marker across the bands. In a variant, the beat frequency of the audio signal may change discontinuously across at least two adjacent bands, with a step change at the boundary between the bands.

As with the embodiment illustrated in FIG. 6, the base station 4; 4' may also be configured to generate a haptic signal corresponding to the marker proximity value. The haptic signal may comprise a series of pulses which have at least the same frequency and optionally the same pulse duty as the second and third parameters of the audio signal.

FIGS. 8A-E show representations of a graphical user interface (GUI) to be output by the base station 4. Five instances of the user interface are shown, corresponding to five different marker proximity values. The five instances correspond to five respective bands in the range of the marker proximity value. The user interface comprises a plurality of user interface elements, including a numerical distance value 61, a marker element 62, a probe element 63 and one or more range band elements 64. The marker element may be a graphical representation of a marker and the probe element may be a graphical representation of a probe.

One or more parameters of each element may be varied in correspondence with a change in the marker proximity value. For example, at least one of a colour (whose aspects may include hue, saturation, tint, shade and tone), transparency, size or position of the element of the graphical interface may be varied. The different shading patterns in FIGS. 8A-E represent different colours.

The distance value 61 shows a distance in millimetres corresponding to the distance between the probe 10; 10' and the marker 6; 6'. It will be appreciated that in other implementations, alternative units of measurement may be employed. As described above, the base station 4; 4' may be configured to determine a marker proximity value based on the input signal received from the probe 10; 10', e.g. based on the amplitude of the input signal. The base station 4; 4' is configured to display a distance corresponding to the marker proximity value. Alternatively, the distance value 61 may be replaced by a signal strength value, as described with respect to FIG. 1.

The marker element 62 represents a position of the marker 6; 6'. According to the embodiment, the position of the marker element 62 is fixed, and the position of the marker 6; 6' is defined as 'zero' distance. The probe element 63 represents a position of the probe 10; 10'. Together with the marker element 62, the probe element 63 depicts the relative position of the probe 10; 10' with respect to the marker 6; 6'. The probe element 63 is configured to move closer to the marker element 62 as the distance between the probe 10; 10' and marker 6; 6' is reduced, as shown in successive FIGS. 8E to 8A. That is, a position parameter of the probe element 63 is varied with a change in the marker proximity value. In an alternative embodiment, the probe element 63 is fixed and the marker element 62 moves to depict the relative position of the marker 6; 6' with respect to the probe 10; 10'. The marker element 63 may be configured to move closer to the probe element 62 as the distance between the probe 10; 10' and marker 6; 6' is reduced. That is, a position parameter of the marker element 63 may be varied with a change in the probe proximity value.

The plurality of range band elements 64 correspond to the plurality—in this case five—of bands in the distance range. Embodiments may be configured with a greater or fewer number of bands, as shown in embodiments above and disclosed herein. The number of range band elements 64 displayed at each instance of the user interface is based on the band in which the marked proximity value currently lies. For example, in Band 3 (FIG. 8C) there are two range band elements 64 displayed and in Band 4 (FIG. 8B) there are three range band elements 64 displayed. A transparency parameter of each range band element 64 is varied discontinuously from 0 to 1 at the respective boundary between adjacent bands.

In addition, a colour parameter of the range band elements 64 is configured to vary with a change in distance between the probe 10; 10' and the marker 6; 6', as indicated by the different shading patterns in FIGS. 8A-E. As shown, the colour parameter is varied discontinuously as the distance at the boundary between each adjacent band.

The user interface can provide the user with a visual output of the distance or determined signal input signal strength. In addition, by discontinuously changing one or parameters of one or more of the displayed visual elements, the user interface can provide a more effective indication of a boundary between adjacent bands. Whereas a distance or signal value must be read and requires the gaze and attention of the user to provide information, an intuitive indication of the boundary can be provided by changing a parameter in this way. For example, a user may register the change in colour of the range band elements 64 in their peripheral vision, or with a quick glance, while maintaining their main focus on the primary task, e.g., a surgical procedure.

In this way, an indication of distance can be provided without diverting the attention or gaze of the surgeon, thus reducing the occurrence of unintended hand movements. The accuracy of the procedure can therefore be improved, and the system can further reduce the risks of (a) incomplete removal of the tumour or lesion, and (b) excessive tissue removal.

FIGS. 9A-E show representations of audio and visual output signals for a further embodiment. According to the embodiment, the distance range is divided into five bands. As the marker proximity value is varied across the five bands, two parameters of the audio signal and two parameters of visual elements of the user interface are changed. A pitch and a beat frequency parameter of the audio signal are varied with changes in the marker proximity value. A position parameter is varied for a probe element in the user interface and a colour parameter is varied for a range band element in the user interface. In this implementation, the distance ranges are: 0—about 5 mm, about 5—about 10 mm, about 10—about 20 mm, about 20—about 30 mm, about 30—about 40 mm, and >about 40 mm, and the bands are coloured red, orange, yellow, green, and blue moving from the marker outwards, as indicated by the respective cross-hatching patterns in FIG. 9A.

In Band 1 shown in FIG. 9E, which represents the greatest distance between the probe 10; 10' and the marker 6; 6', the pitch of the audio signal is configured to increase proportionally with increasing proximity between the probe 10; 10' and the marker 6; 6'. The beat frequency of the audio signal is constant at zero, i.e., there are no beats. The probe element of the user interface is displayed at the furthest distance from the marker element of the user interface, and the position of the probe element is changed continuously to reduce the distance between the probe element and the marker element with increasing proximity between the probe 10; 10' and the marker 6; 6'. The range band element of the user interface comprises five bands, corresponding to the five bands in the distance range. In Band 1, four of the five bands are displayed without colour (i.e., desaturated to greyscale) as indicated by shading patterns, and one band, corresponding to Band 1, is displayed with colour, as indicated by the cross-hatching pattern.

At the boundary between Band 1 and Band 2, there is no discontinuity in the pitch of the audio signal. The pitch of the audio signal continues to increase linearly across Band 2. There is a discontinuous change in the beat frequency of the audio signal at the boundary between Band 1 and Band 2. There is a step increase in the beat frequency to a low initial value, followed by a linear increase in beat frequency across Band 2. The position of the probe element continues to change continuously to reduce the distance between the probe element and the marker element across Band 2, as shown in FIG. 9D. Two bands of the five bands in the range band element are displayed with colour in Band 2, as indicated by the respective cross-hatching patterns.

At the boundary between Band 2 and Band 3, there is a step increase in the pitch of the audio signal. The pitch of the audio signal continues to increase linearly across Band 3. There is a step increase in the beat frequency of the audio signal at the boundary between Band 2 and Band 3, and a linear increase in beat frequency across Band 3. The position of the probe element continues to change continuously to reduce the distance between the probe element and the marker element across Band 3, as shown in FIG. 9C. Three bands of the five bands in the range band element are displayed with colour in Band 3, as indicated by the respective cross-hatching patterns.

At the boundary between Band 3 and Band 4, there is a step increase in the pitch of the audio signal. The pitch of the audio signal remains constant across Band 4. There is a step decrease in the beat frequency of the audio signal at the boundary between Band 3 and Band 4. The beat frequency is decreased to zero and remains constant at zero, i.e., there are no beats. The position of the probe element continues to change continuously to reduce the distance between the probe element and the marker element across Band 4, as shown in FIG. 9B. Four bands of the five bands in the range band element are displayed with colour in Band 4, as indicated by the respective cross-hatching patterns.

At the boundary between Band 4 and Band 5, there is a step increase in the pitch of the audio signal. The pitch of the audio signal remains constant across Band 5. There is no change in the beat frequency of the audio signal, which remains constant at zero, i.e., there are no beats. The position of the probe element continues to change continuously to reduce the distance between the probe element and the marker element across Band 5, as shown in FIG. 9A. All five bands of the range band element are displayed with colour in Band 5.

FIGS. 9A-E illustrate how various parameters of the audio and visual output of the base station can be varied continuously and/or discontinuously based on band in the distance range, so as to give a clear and intuitive indication of the current range band to the user of the system. The signals can be utilised in combination to discern accurately the relative locations of the probe 10; 10' and the marker 6; 6', without diverting the full attention of a user away from the task at hand. In this way, the system can provide improved accuracy of probe positioning with respect to the marker, improving the efficiency and effectiveness of such surgical procedures.

Although the number of bands shown in FIGS. 9A-E is five, it will be understood that the number of bands chosen may depend on the overall distance range and the distance covered by each band. The overall distance range may be from about 40 mm to about 80 mm and in some examples may be about 40 mm or about 50 mm or about 60 mm. The distance covered by each band may be any division of the overall range and may relate to the level of precision that the user requires. The distance covered by each band may also be selected to limit the amount of information that the user has to interpret so that the complexity of the interface is kept to a minimum. In this way, the bands can provide useful information to the user. The numerical display may tell the user the distance in millimetres or other suitable units and may therefore provide an additional level of precision if needed. The bands provided are thus configured for sufficient granularity of information so that the user can tell rapidly by looking or via the audio a) that the probe is moving towards or away from the marker and b) an approximate indication of the distance between the probe and the marker. Selecting the number of bands to be 8 or fewer may be an advantage because a greater number of bands might be more difficult to distinguish rapidly from each other. In some cases, e.g. for a precise excision, the bands may be less than about 5 mm in size, for example about 2 or about 4 mm. Alternatively, the bands may be between about 5 and about 20 mm in size, and may be about 5 or about 10 mm in size.

The required precision may increase as the probe gets closer to the marker and it may be desirable for the size of the bands to decrease as the probe gets closer to the marker. For example, the bands further from the marker may be up to 20 mm in size (width) but may decrease in size closer to the marker where they may be 5 mm or less in size.

In the embodiment shown in FIGS. 8A-E, the bands are constant in size at about 10 mm, meaning that the ranges are 0-about 10 mm, about 10-about 20 mm, about 20-about 30 mm, about 30-about 40 mm, and >40 mm. In the embodiment shown in FIGS. 9A-E, the bands start at 10 mm in size and then reduce to 5 mm closer to the marker, meaning that the ranges are about 0-about 5 mm, about 5-about 10 mm, about 10-about 20 mm, about 20-about 30 mm, about 30-about 40 mm, and >about 40 mm. The probe may be initially outside the overall range, i.e. the probe is further from the marker than the limit of the range, and so the furthest part of the range may be indicated using a 'greater than' sign (>) to show that the probe is outside the range illustrated in the graphical display.

The markers of the detection system described herein may each comprise one or more lengths of material ("magnetic marker material") which may give a linear response or a harmonic/non-linear response to an alternating magnetic field. The marker may exhibit a large Barkhausen discontinuity in the magnetisation curve and may be formed from e.g. iron-, cobalt- and nickel-rich glass-coated amorphous microwires, iron-silicon-boron based amorphous microwires, iron-cobalt based amorphous microwires, or bulk metallic glass wires.

In some embodiments, the length or lengths of magnetic marker material may comprise a length of solid wire; a glass-coated microwire with core diameter between, e.g., about 5 and about 100 micrometres and a coating thickness of between, e.g., about 0.5 and about 40 micrometres; a bundle of lengths of solid wire or glass-coated microwire; or a hollow tube.

Any of the markers may comprise more than one piece of magnetic marker material together with additional material to join or enclose the pieces of magnetic marker material and form the final shape of the marker. The marker may comprise a tube, tubes or a complete or partial shell of another material within which the lengths of magnetic material of the marker are held. The magnetic material may also be coated or enclosed within a further biocompatible material.

For example, the tube or shell containing the magnetic marker material comprises a biocompatible plastically deformable material such as a 316 stainless steel, Titanium, Titanium alloy or similar.

In some embodiments, the drive unit may comprise one or more drive coils. Alternatively, an alternating magnetic field may be generated by, for example, a spinning permanent magnet.

The sensing unit may comprise one or more sense coils or, alternatively, a solid-state magnetometer. In some implementations, the sense unit may comprise, e.g., a Hall effect sensor, mems sensor, magneto-transistor/magneto-diode, or a 'squid' magnetometer.

The drive frequency of the magnetic field may be in the range about 100 Hz to about 100 kHz. Higher frequencies towards about 100 kHz may be advantageous to maximise the sensed signal. A higher frequency may also allow more cycles per second to be averaged during detection to improve noise suppression while still delivering a 'real time' output to the user i.e. updating the output signal at least about 10 times per second. Hence for noise suppression a frequency of at least about 1000 Hz and preferably at least about 10 kHz may be desirable. In order to give an apparent 'real time' response to the user, the output may need to update at least every about 0.1 s. A frequency of 1 kHz allows about 100 cycles to be averaged between each update to the user, and about 10 kHz allows about 1000 cycles to be averaged between each update to the user.

Advantages may also be gained from a lower drive frequency, and these include reduced eddy current losses both in the marker (in cases where it is prone to eddy currents for example if it has high conductivity) and from the surrounding tissue. For reduced eddy current losses, a frequency of less than about 30 kHz may be advantageous. In the operating room environment, electromagnetic interference signals may be more frequently experienced at frequencies above about 100 kHz and therefore choosing a drive frequency such that the harmonics of interest are less than about 100 kHz may be beneficial.

While various details have been set forth in the foregoing description, it will be appreciated that the various aspects of the techniques for operating a diagnostic and/or surgical guidance system suitable for identifying, localizing, tracking, and detecting position of one or more implanted markers may be practiced without these specific details. One skilled in the art will recognize that the herein described components (e.g., operations), devices, objects, and the discussion accompanying them are used as examples for the sake of conceptual clarity and that various configuration modifications are contemplated. Consequently, as used herein, the specific exemplars set forth and the accompanying discussion are intended to be representative of their more general classes. In general, use of any specific exemplar is intended to be representative of its class, and the non-inclusion of specific components (e.g., operations), devices, and objects should not be taken limiting.

Further, while several forms have been illustrated and described, it is not the intention of the applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

For conciseness and clarity of disclosure, selected aspects of the foregoing disclosure have been shown in block diagram form rather than in detail. Some portions of the detailed descriptions provided herein may be presented in terms of instructions that operate on data that is stored in one or more computer memories or one or more data storage devices of the base station or the one or more processors or microprocessors operative therein (e.g. floppy disk, hard disk drive, caches, random access memory, and other optical and magnetic storage devices and media). Such descriptions and representations are used by those skilled in the art to describe and convey the substance of their work to others skilled in the art. In general, an algorithm refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states. The various methods steps disclosed herein may be implemented or programmed as algorithms, data structures, and instructions that may operate upon inputs from data channels and generate outputs that contain various types of data such as user actional data, user feedback signals, information, and images.

Unless specifically stated otherwise as apparent from the foregoing disclosure, it is appreciated that, throughout the foregoing disclosure, discussions using terms such as "processing" or "computing" or "calculating" or "determining" or "displaying" or the like, refer to the action and processes of a computer system, processor-based base station, or similar electronic computing device, that manipulates and transforms data represented as physical (electronic) quantities within the computer system's registers and memories into other data similarly represented as physical quantities within the computer system memories or registers or other such information storage, transmission or display devices.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analogue or digital fashion or some combination thereof.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. In one form, several portions of the subject matter described herein may be implemented via an application specific integrated circuits (ASIC), a field programmable gate array (FPGA), a digital signal processor (DSP), or other integrated formats. However, those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure.

In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analogue communication medium (e.g., a fibre optic cable, a waveguide, a wired communications link, a wireless communication link (e.g., transmitter, receiver, transmission logic, reception logic, etc.), etc.).

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

The terms "approximately" and "about" may be used to mean within +20% of a target value in some embodiments, within +10% of a target value in some embodiments, within +5% of a target value in some embodiments, and yet within +2% of a target value in some embodiments. The terms "approximately" and "about" may include the target value.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

The use of headings and sections in the application is not meant to limit the disclosure; each section can apply to any aspect, embodiment, or feature of the disclosure. Only those claims which use the words "means for" are intended to be interpreted under 35 USC 112, sixth paragraph. Absent a recital of "means for" in the claims, such claims should not be construed under 35 USC 112. Limitations from the specification are not intended to be read into any claims, unless such limitations are expressly included in the claims.

Embodiments disclosed herein may be embodied as a system, method or computer program product. Accordingly, embodiments may take the form of an entirely hardware embodiment, an entirely software embodiment (including firmware, resident software, micro-code, etc.) or an embodiment combining software and hardware aspects that may all generally be referred to herein as a "circuit," "module," or "system." Furthermore, embodiments may take the form of a computer program product embodied in one or more computer readable medium(s) having computer readable program code embodied thereon.

Although aspects of the invention herein have been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the scope of the invention as defined by the appended claims.

The invention claimed is:

1. A computer implemented method of detecting a marker in a body, comprising:
   receiving, by a processor, an input signal from a probe, where the input signal is generated by a probe in response to detecting a marker signal from the marker;
   determining, by the processor, a marker proximity value based on the input signal, where the marker proximity value corresponds to a distance between the probe and the marker;
   generating, by the processor and for output by a user interface device, at least one feedback signal based on the marker proximity value,
      wherein a range of the marker proximity value is divided into a plurality of predetermined distance bands;
      wherein the plurality of bands comprises at least 3 bands;
      wherein at least one parameter of the feedback signal is varied in relation to the marker proximity value; and
   wherein the at least one parameter of the feedback signal, or a rate of change of at least one parameter of the feedback signal in relation to the marker proximity value, is varied discontinuously at at least one boundary between two adjacent bands of the plurality of bands;
      wherein another parameter of the feedback signal is increased progressively in relation to the marker proximity value across more than one band of the plurality of bands and is varied continuously across more than one boundary between adjacent bands of the plurality of bands; and
   outputting, by the user interface device, the generated feedback signal.

2. The method of claim 1, for each of the plurality of bands independently, the at least one parameter of the feedback signal is configured to (a) vary linearly with a change in the marker proximity value within the band, (b) vary non-linearly with a change in the marker proximity value within the band, or (c) remain substantially constant with a change in the marker proximity value within the band.

3. The method of claim 1, wherein, for at least a first band, a first parameter of the feedback signal is varied continuously with a change in the marker proximity value within the band and, for at least a second band different from the first band, a second parameter of the feedback signal is varied continuously with a change in the marker proximity value within the band.

4. The method of claim 1, wherein a first parameter of the feedback signal is configured to remain substantially constant within at least one of the bands;
   wherein optionally the first parameter is a pulse frequency, a pulse length and/or a pulse duty cycle of the feedback signal.

5. The method of claim 4, wherein another parameter of the feedback signal is an amplitude of the signal.

6. The method of claim 5, wherein the feedback signal is an audio signal and the another parameter of the signal is a pitch and/or volume of the signal.

7. The method of claim 5 wherein a still further parameter of the feedback signal is varied in relation to the marker proximity value; and wherein the at least one parameter is the pulse length or duty cycle of the signal, and the still further parameter is the pulse frequency; and optionally further wherein the still further parameter is varied continuously in relation to the marker proximity value within at least one band; or configured to remain substantially constant with respect to the marker proximity value within at least one band.

8. The method of claim 1, wherein a still further parameter is varied discontinuously at at least one boundary between two adjacent bands of the plurality of bands.

9. The method of claim 1, wherein the user interface device comprises a speaker, and the feedback signal comprises an audio signal; wherein the at least one parameter is optionally selected from an amplitude, tone, pitch, timbre, beat frequency or beat pattern of the audio signal.

10. The method claim 1, wherein the user interface device comprises a haptic feedback device, and the feedback signal comprises a haptic signal, optionally wherein the haptic feedback device comprises a selectively operable haptic actuator.

11. The method of claim 1, wherein the plurality of bands comprises between 3 and 8 bands.

12. The method of claim 1, wherein the marker proximity value corresponding to at least one boundary between two adjacent bands is user-defined.

13. The method of claim 1, wherein the feedback signal further comprises an alert at one or more boundaries between two adjacent bands.

14. The method of claim 1, further comprising:
   generating, by the processor and for output by a display, a graphical interface based on the marker proximity value;
      wherein at least one parameter of at least one element of the graphical interface) varies in relation to the marker proximity value;
      wherein the at least one parameter of at least one element of the graphical interface or a rate of change of the at least one parameter in relation to the marker proximity value, is varied discontinuously at a boundary between two adjacent bands of the plurality of bands;
      wherein, optionally, at least one element of the graphical interface comprises a representation of a probe and its proximity to a marker; and
   outputting, by the display, the generated graphical interface.

15. The method of claim 8, wherein, for each of the plurality of bands, the at least one parameter of the graphical interface element is configured independently to (a) vary linearly with a change in the marker proximity value within the band, (b) vary non-linearly with a change in the marker proximity value within the band, or (c) remain constant with a change in the marker proximity value within the band.

16. The method of claim 8, wherein, for at least a first band, a parameter of a first element of the graphical interface is varied continuously with a change in the marker proximity value within the band and, for at least a second band different from the first band, a parameter of a second element of the graphical interface is varied continuously with a change in the marker proximity value within the band.

17. A non-transitory computer-readable medium comprising instructions which, when executed by a processor, cause the processor to perform the method of claim 1.

18. A system for detecting a marker in a body, comprising:
a probe comprising a sensor, configured to generate an input signal in response to detecting a marker signal from the marker; and
a base station comprising one or more processors and a memory, wherein the memory is stores instructions which, when executed by the one or more processors, cause the base station to perform the method of claim 1.

19. A computer implemented method of detecting a marker in a body, comprising:
receiving, by a processor, an input signal from a probe, where the input signal is generated by a probe in response to detecting a marker signal from the marker;
determining, by the processor, a marker proximity value based on the input signal, where the marker proximity value corresponds to a distance between the probe and the marker;
generating, by the processor and for output by a user interface device, at least one audio signal based on the marker proximity value,
wherein a range of the marker proximity value is divided into a plurality of predetermined distance bands;
wherein a pulse duty cycle or pulse length of the audio signal is varied discontinuously at at least one boundary between two adjacent bands of the plurality of bands, and wherein a pitch of the audio signal is increased progressively in relation to the marker proximity value across more than one band and varied continuously across more than one boundary between adjacent bands of the plurality of bands, and wherein the rate of change of the pitch of the audio signal in relation to the marker proximity value is varied discontinuously at at least one boundary between two adjacent bands of the plurality of bands, and wherein a pulse frequency of the audio signal is varied continuously in relation to the marker proximity value within at least one band; and outputting, by the user interface device, the generated audio signal.

* * * * *